United States Patent
Maa et al.

(10) Patent No.: US 6,284,282 B1
(45) Date of Patent: Sep. 4, 2001

(54) METHOD OF SPRAY FREEZE DRYING PROTEINS FOR PHARMACEUTICAL ADMINISTRATION

(75) Inventors: Yuh-Fun Maa, Millbrae; Phuong-Anh Nguyen, San Mateo, both of CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/299,377

(22) Filed: Apr. 27, 1999

Related U.S. Application Data
(60) Provisional application No. 60/145,738, filed on Apr. 29, 1998.

(51) Int. Cl.$^7$ ............................... A61K 9/14; A61K 9/10; A61K 38/16
(52) U.S. Cl. ........................... 424/499; 424/489; 424/45; 424/46; 514/2; 514/12; 514/13
(58) Field of Search ............................... 424/45, 489, 46, 424/499; 514/2, 12, 13

(56) References Cited

U.S. PATENT DOCUMENTS

| | | |
|---|---|---|
| 4,477,492 | 10/1984 | Bergna et al. . |
| 5,019,400 | 5/1991 | Gombotz et al. . |
| 5,260,306 | 11/1993 | Boardman et al. . |
| 5,354,562 * | 10/1994 | Platz et al. ........................... 424/489 |
| 5,354,654 | 10/1994 | Ligler et al. . |
| 5,589,167 * | 12/1996 | Cleland et al. ...................... 424/85.7 |
| 5,891,478 * | 4/1999 | Johnson et al. ...................... 424/502 |
| 5,952,008 * | 10/1999 | Backstrom et al. .................. 424/499 |

FOREIGN PATENT DOCUMENTS

| | | |
|---|---|---|
| 308238A1 | 3/1989 | (EP) . |
| 440989A1 | 8/1991 | (EP) . |
| 312052B1 | 1/1994 | (EP) . |
| 440989B1 | 4/1995 | (EP) . |
| WO 90/13285 | 11/1990 | (WO) . |
| WO 91/16882 | 11/1991 | (WO) . |
| WO 93/13752 | 7/1993 | (WO) . |
| WO 95/18635 | 7/1995 | (WO) . |
| WO 95/31479 | 11/1995 | (WO) . |
| WO 96/40076 | 12/1996 | (WO) . |
| WO 97/35562 | 10/1997 | (WO) . |
| WO 97/41833 | 11/1997 | (WO) . |
| WO 97/44013 | 11/1997 | (WO) . |

OTHER PUBLICATIONS

Heller et al Biotechnol. Prog. 1997, 13, 590–596.*
Edwards et al. Science. 1997;276:1868–1871.*
Arakawa and Timasheff, "Preferential interactions of proteins with solvent components in aqueous amino acid solutions" *Archives of Biochemistry & Biophysics* 224(1):169–177 (Jul. 1, 1983).
Arakawa and Timasheff, "Stabilization of protein structure by sugars" *Biochemistry* 21(25):6536–6544 (Dec. 7, 1982).
Broadhead et al., "The effect of process and formulation variables on the properties of spray–dried β–galactosidase" *Journal of Pharmacy & Pharmacology* 46(6):458–467 (Jun. 1994).
Carpenter et al., "Modes of Stabilization of a Protein by Organic Solutes during Desiccation" *Cryobiology* 25:459–470 (1988).
Carpenter et al., "Separation of freezing– and drying–induced denaturation of lyophilized proteins using stress–specific stabilization. I. Enzyme activity and calorimetric studies" *Archives of Biochemistry & Biophysics* 303(2):456–464 (Jun. 1993).

(List continued on next page.)

Primary Examiner—Diana Dudash
Assistant Examiner—Shahnam Sharareh
(74) Attorney, Agent, or Firm—Craig G. Svoboda

(57) ABSTRACT

The present invention relates to the spray freeze dry preparation of dry powder formulations of therapeutic proteins suitable for administration via pulmonary delivery.

15 Claims, 10 Drawing Sheets

OTHER PUBLICATIONS

Carpenter et al., "The Mechanism of Cryoprotection of Proteins by Solutes" *Cryobiology* 25:244–255 (1988).

Chan et al., "Spray dried powders and powder blends of recombinant human deoxyribonuclease (rhDNase) for aerosol delivery" *Pharmaceutical Research* 14(4):431–437 (Apr. 1997).

Chang et al., "Surface–induced denaturation of proteins during freezing and its inhibition by surfactants" *Journal of Pharmaceutical Sciences* 85(12):1325–1330 (Dec. 1996).

Chilson et al., "Effects of freezing on enzymes" Federation Proceedings 24(2):S55–S65 (1965).

Costantino et al., "Aggregation of a lyophilized pharmaceutical protein, recombinant human albumin: effect of moisture and stabilization by excipients" *Bio/Technology* 13(5):493–496 (May 1995).

Crowe et al., "Are Freezing and Dehydration Similar Vectors? A Comparison of Modes of Interaction of Stabilizing Solutes with Biomolecules" *Cryobiology* 27:219–231 (1990).

Eckhardt et al., "Effect of freezing on aggregation of human growth hormone" *Pharmaceutical Research* 8(11):1360–1364 (Nov. 1991).

Edwards et al., "Large porous particles for pulmonary drug delivery" *Science* 276(5320):1868–1871 (Jun. 20, 1997).

Hsu et al., "Surface denaturation at solid–void interface—a possible pathway by which opalescent particulates form during the storage of lyophilized tissue–type plasminogen activator at high temperatures" *Pharmaceutical Research* 12(1):69–77 (Jan. 1995).

Izutsu et al., "Decreased protein–stabilizing effects of cryoprotectants due to crystallization" *Pharmaceutical Research* 10(8):1232–1237 (Aug. 1993).

Izutsu et al., "Effect of mannitol crystallinity on the stabilization of enzymes during freeze–drying" *Chemical & Pharmaceutical Bulletin* 42(1):5–8 (Jan. 1994).

Izutsu et al., "Stabilization of β–galactosidase by amphiphilic additives during freeze–drying" *International Journal of Pharmaceutics* 90:187–194 (1993).

Izutsu et al., "The effects of additives on the stability of freeze–dried β–galactosidase stored at elevated temperature" *Intl. J. Pharmaceutics* 71:137–146 (1991).

Maa et al., "Effect of spray drying and subsequent processing conditions on residual moisture content and physical/biochemical stability of protein inhalation powders" *Pharmaceutical Research* 15(5):768–775 (May 1998).

Maa et al., "Protein Denaturation by Combined Effect of Shear and Air–Liquid Interface" *Biotechnology and Bioengineering* 54(6):503–512 (Jun. 20, 1997).

Maa et al., "Spray–drying of air–liquid interface sensitive recombinant human growth hormone" *Journal of Pharmaceutical Sciences* 87(2):152–159 (Feb. 1998).

Miki et al., "Difference in inhaled aerosol deposition patterns in the lungs due to three different sized aerosols" *Nuclear Medicine Communications* 13(7):553–562 (Jul. 1992).

Mitchell et al., "Effect of particle size of bronchodilator aerosols on lung distribution and pulmonary function in patients with chronic asthma" *Thorax* 42(6):457–461 (Jun. 1987).

Mumenthaler et al., "Feasibility Study on Spray–Drying Protein Pharmaceuticals: Recombinant Human Growth Hormone and Tissue–Type Plasminogen Activator" *Pharm. Res.* 11:12–20 (1994).

Nema and Avis, "Freeze–thaw studies of a model protein, lactate dehydrogenase, in the presence of cryoprotectants" *Journal of Parenteral Science & Technology* 47(2):76–83 (Mar.–Apr. 1993).

Prestrelski et al., "Separation of freezing– and drying–induced denaturation of lyophilized proteins using stress–specific stabilization. II. Structural studies using infrared spectroscopy" *Archives of Biochemistry & Biophysics* 303(2):465–473 (Jun. 1993).

Shikama et al., "Denaturation of Catalase by Freezing and Thawing" *Nature* 190(4770):83–84 (Apr. 1, 1961).

Strambini and Gabellieri, "Proteins in frozen solutions: evidence of ice–induced partial unfolding" *Biophysical Journal* 70(2):917–976 (Feb. 1996).

Tamiya et al., "Freeze denaturation of enzymes and its prevention with additives" *Cryobiology* 22(5):446–456 (Oct. 1985).

Townsend and DeLuca, "Use of lyoprotectants in the freeze–drying of a model protein, ribonuclease A" *Journal of Parenteral Science & Technology* 42(6):190–199 (Nov.–Dec. 1988).

Watanabe et al., "Protective Effects of Non–ionic Surfactants against Denaturation of Rabbit Skeletal Myosin by Freezing and Thawing" *Agricultural and Biological Chemistry* 52(10):2517–2523 (1988).

Winters et al., "Precipitation of proteins in supercritical carbon dioxide" *Journal of Pharmaceutical Sciences* 85(6):586–594 (Jun. 1996).

Yeo et al., "Formation of Microparticulate Protein Powders Using a Supercritical Fluid Antisolvent" *Biotechnology and Bioengineering* 41:341–346 (1993).

* cited by examiner

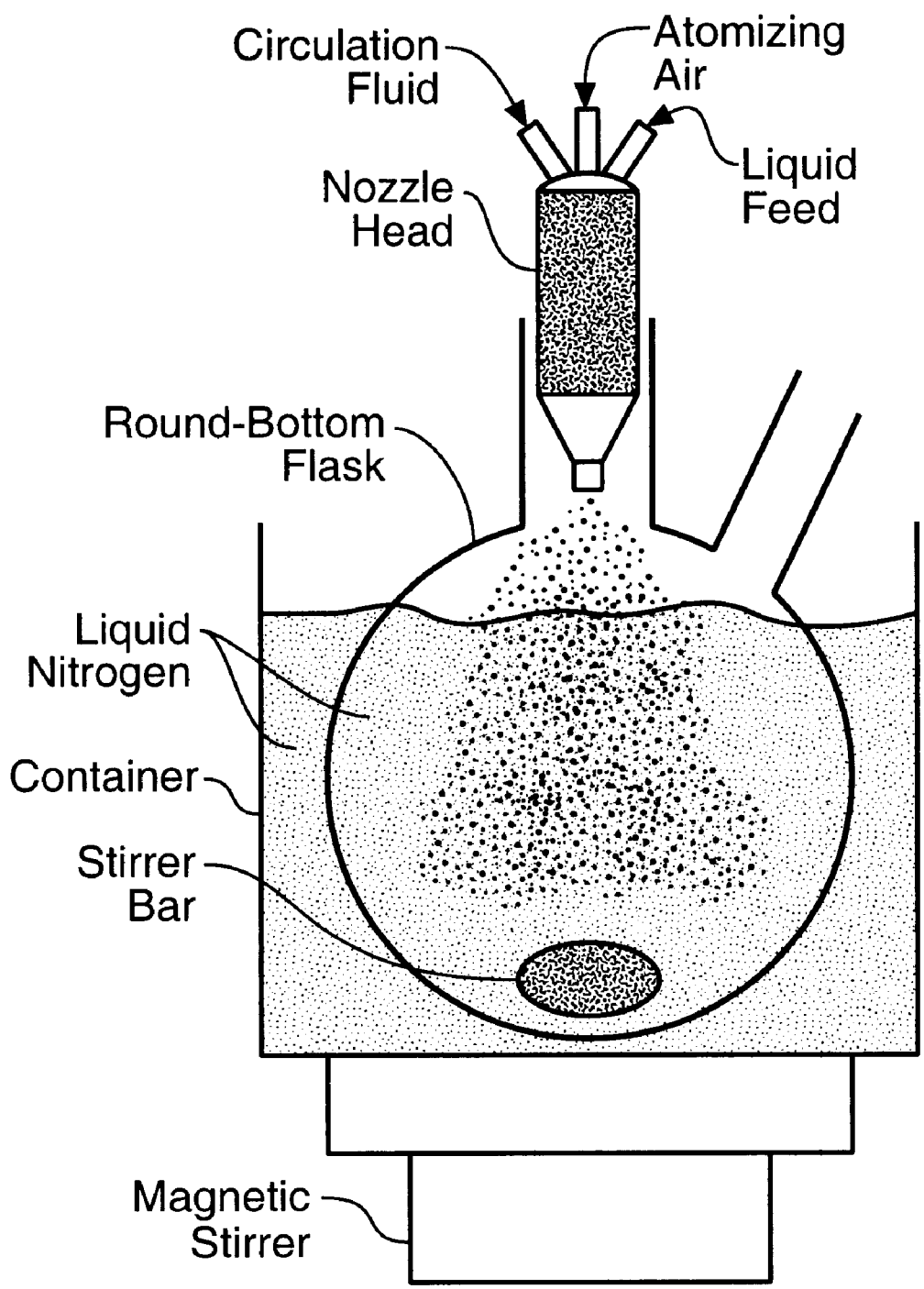
FIG._1

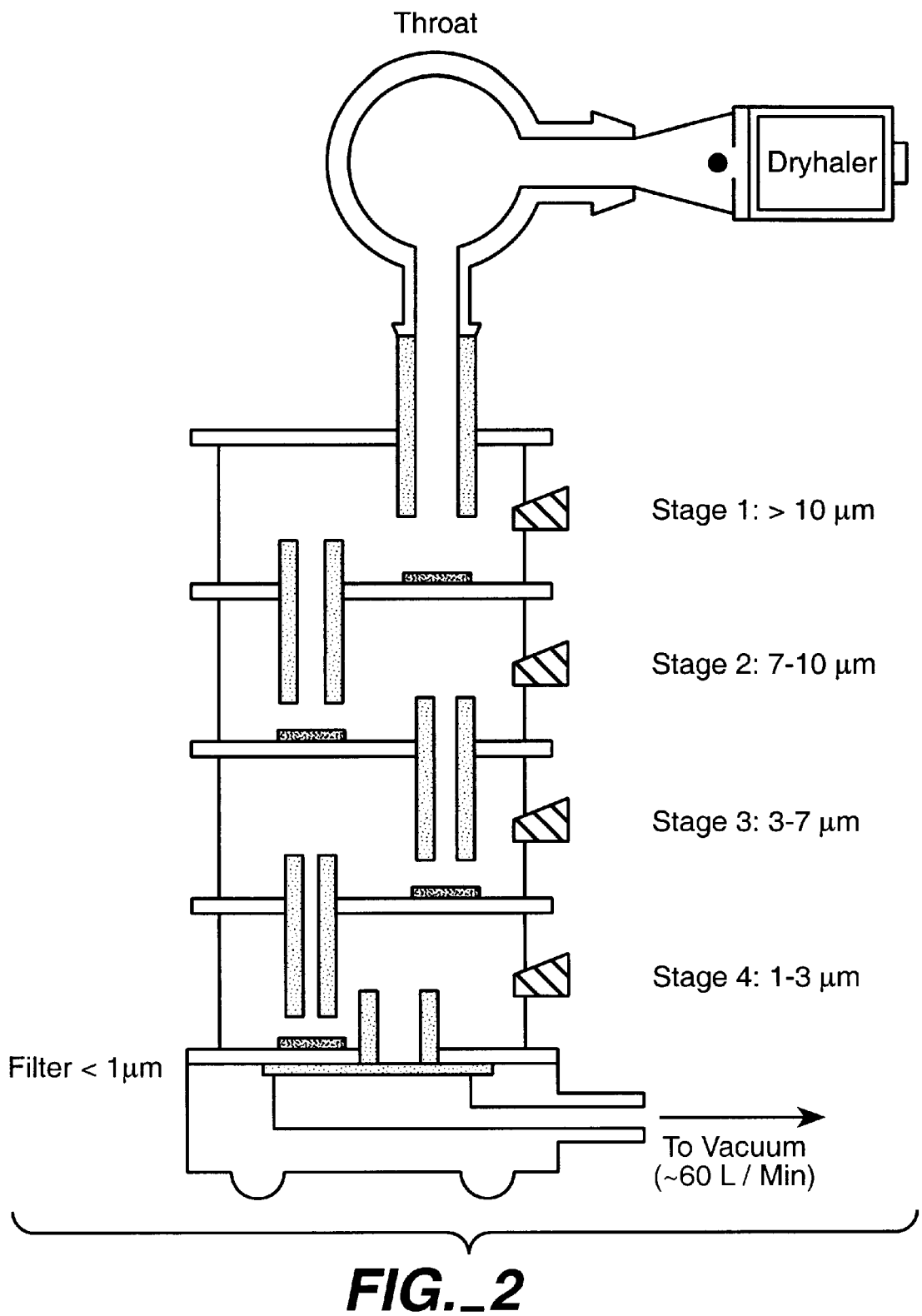
FIG._2

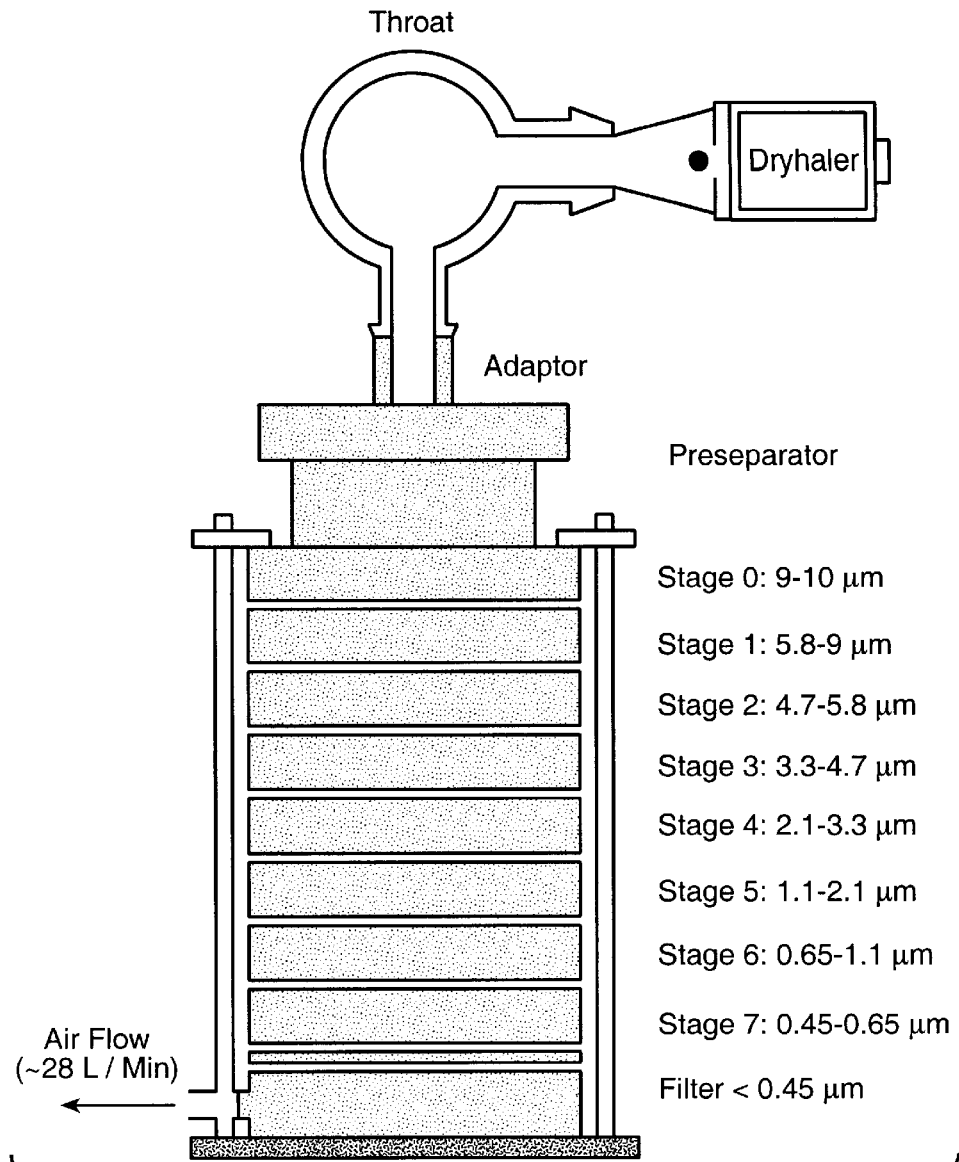
FIG._3A
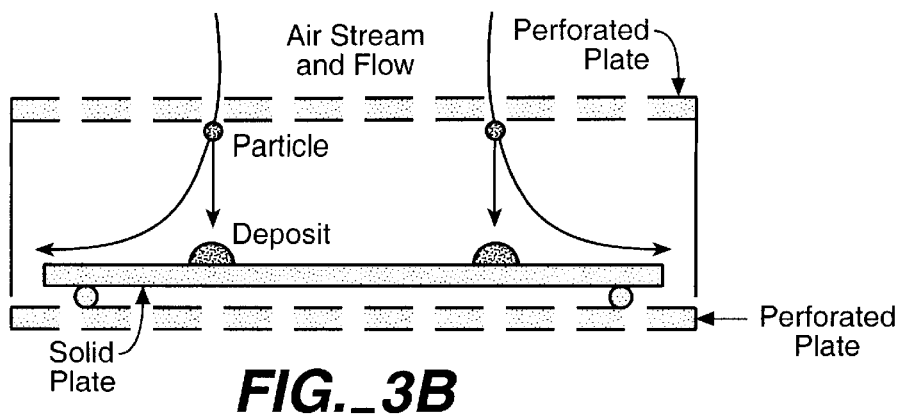
FIG._3B

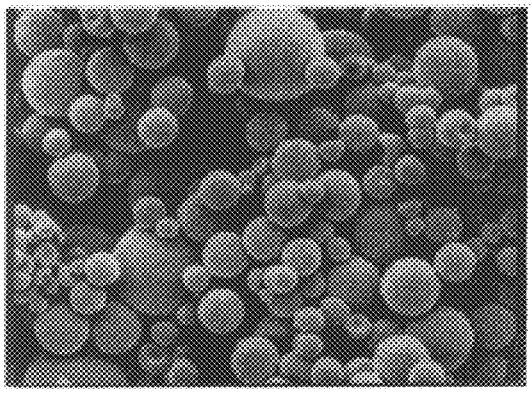
FIG._4A
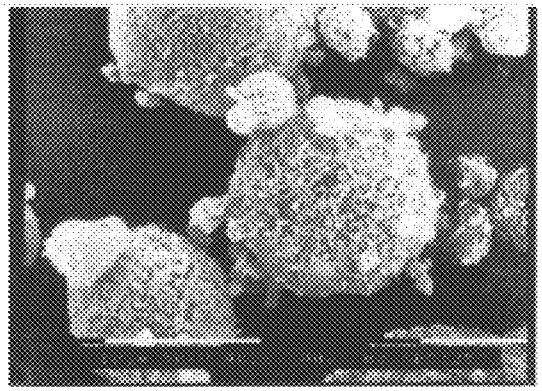
FIG._4B
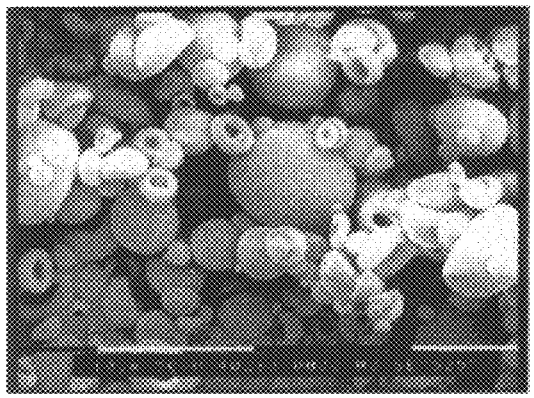
FIG._4C
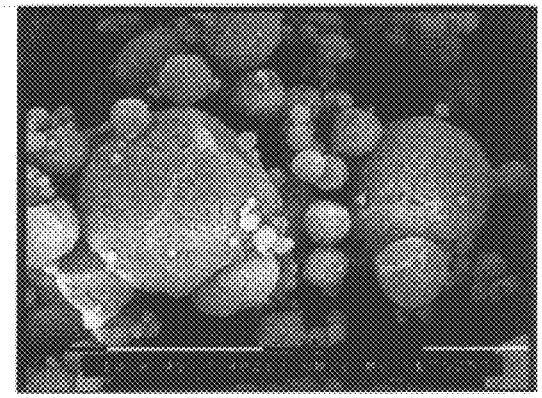
FIG._4D

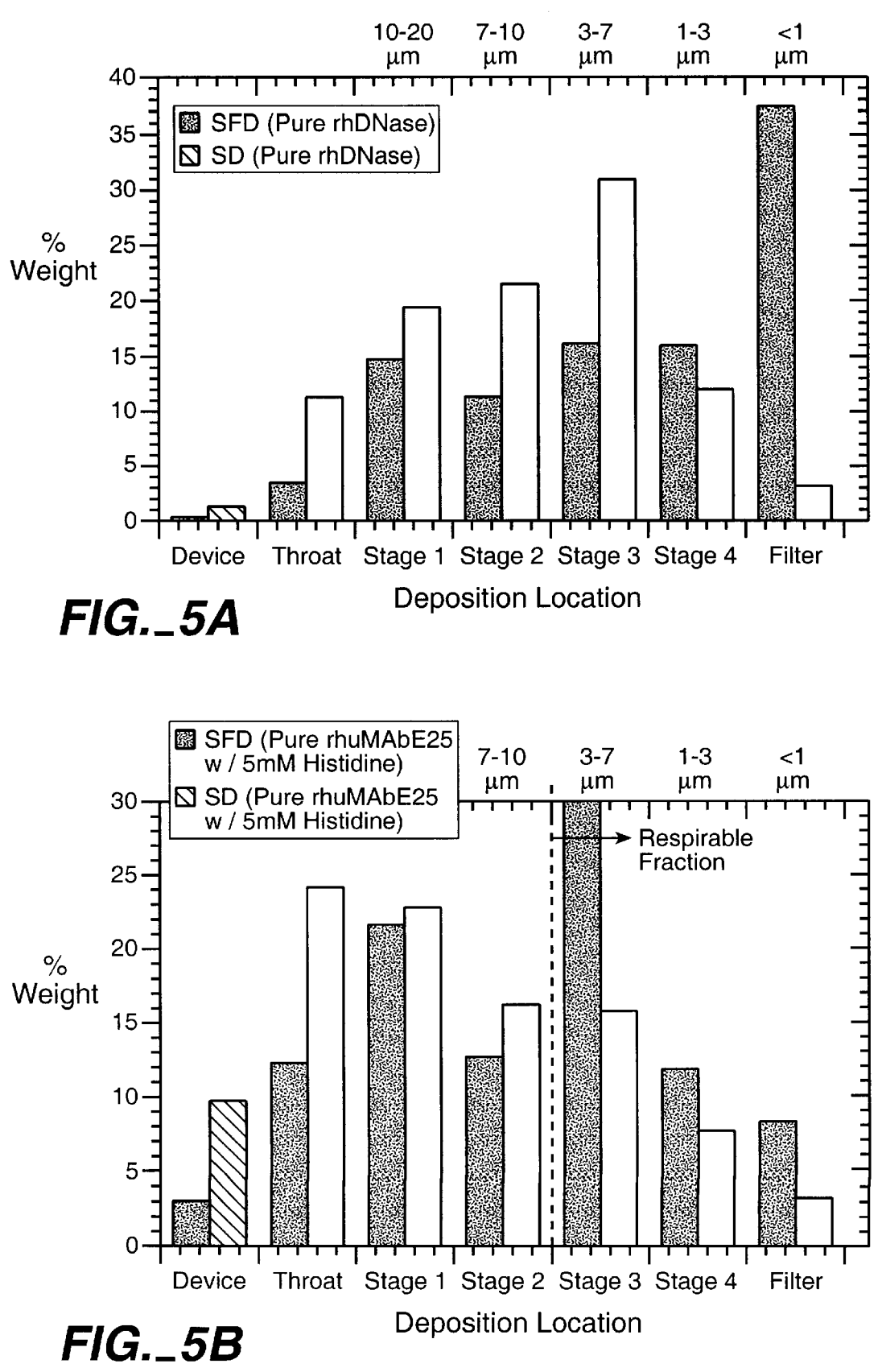

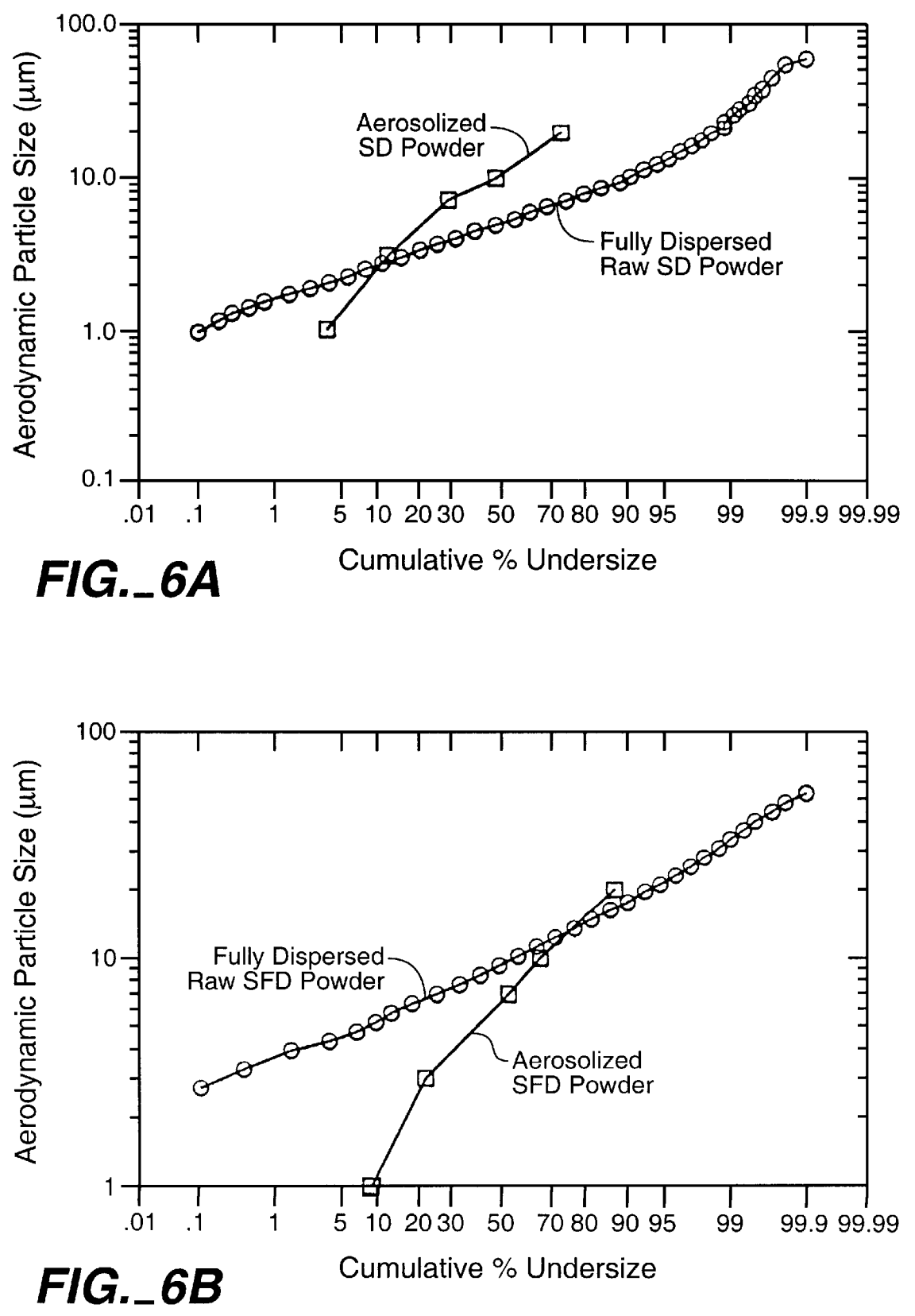

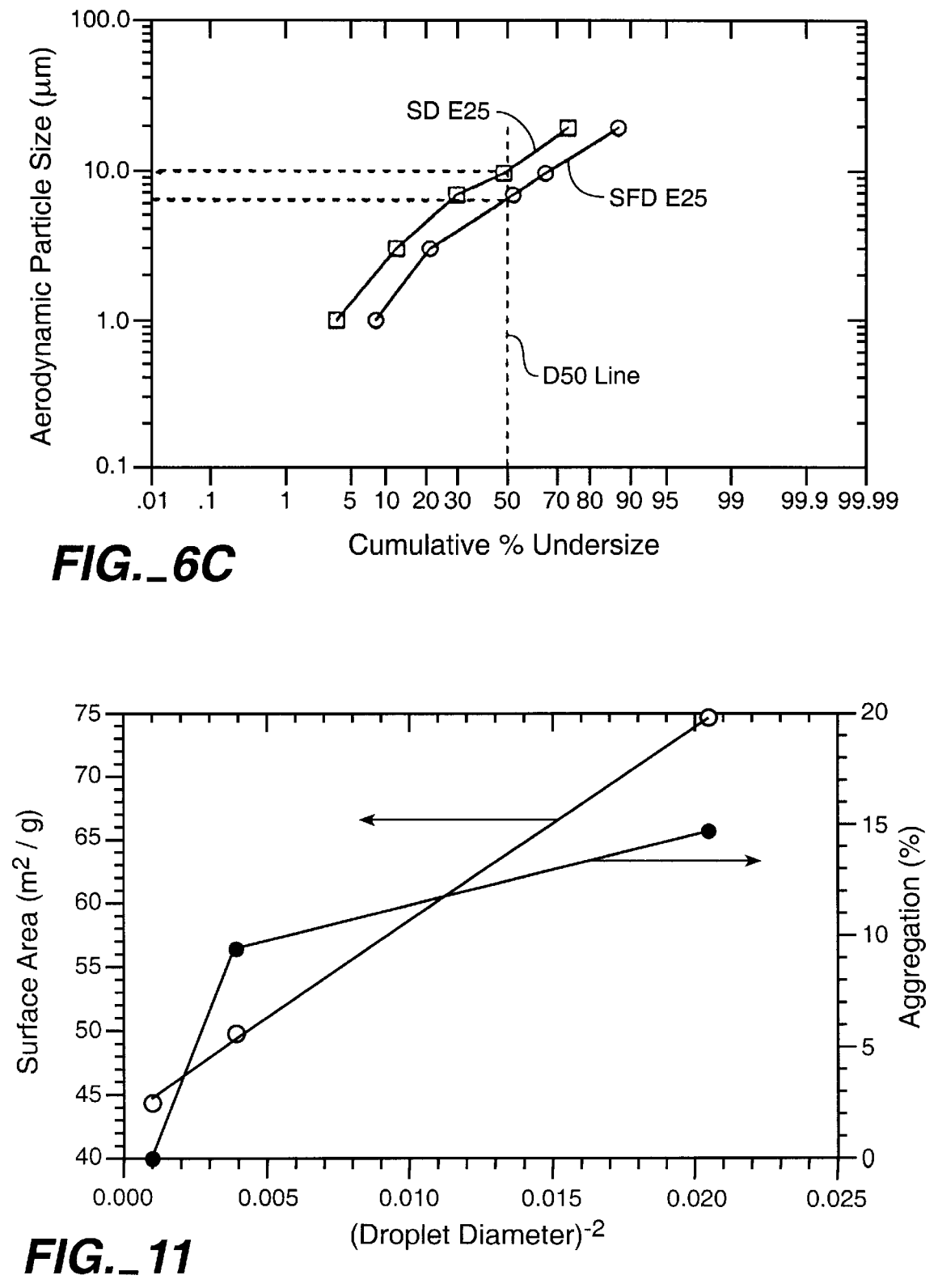

*FIG._7A*
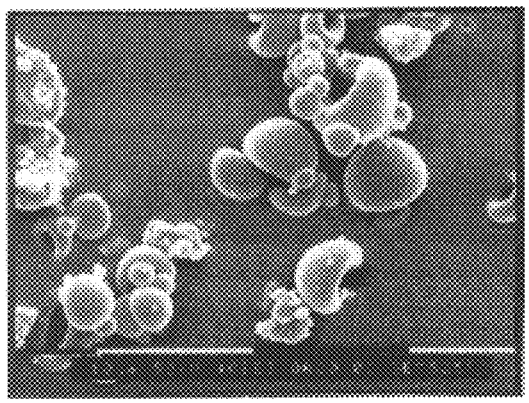
*FIG._7B*
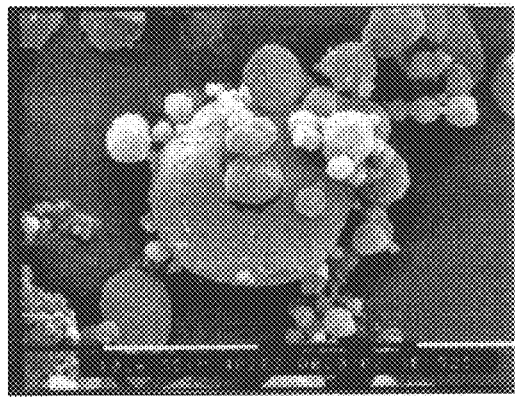
*FIG._7C*
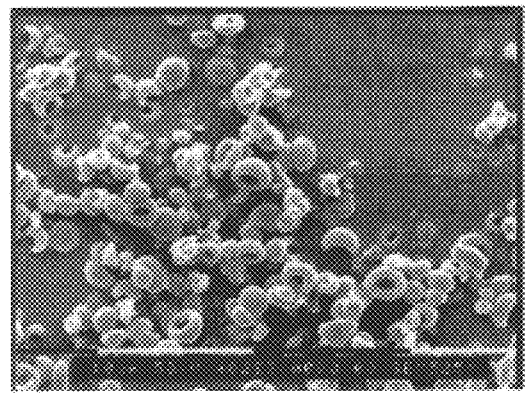
*FIG._7D*
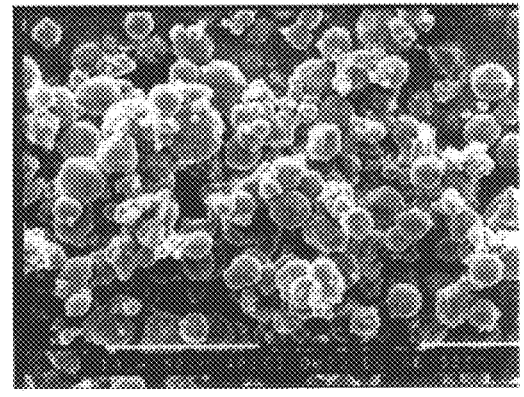

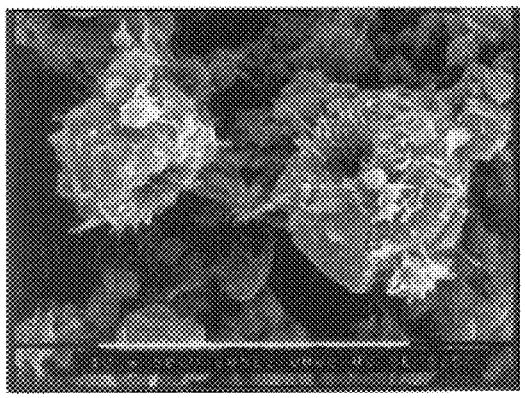
*FIG._8A*
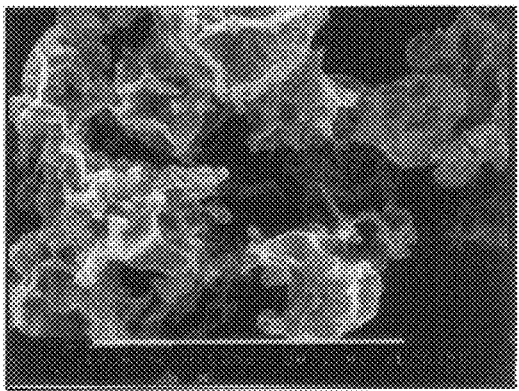
*FIG._8B*
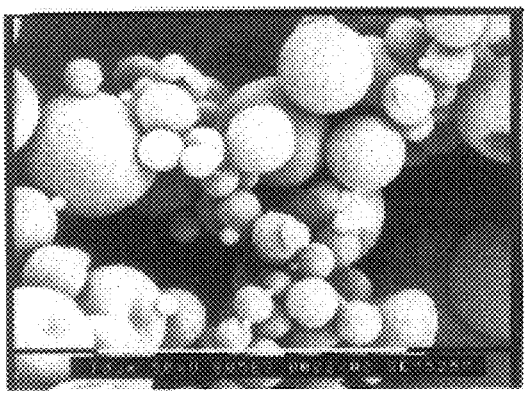
*FIG._8C*
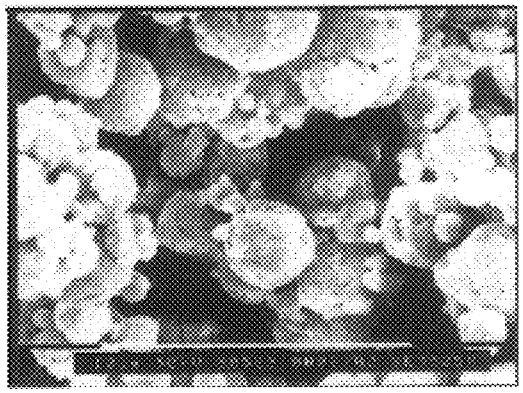
*FIG._8D*
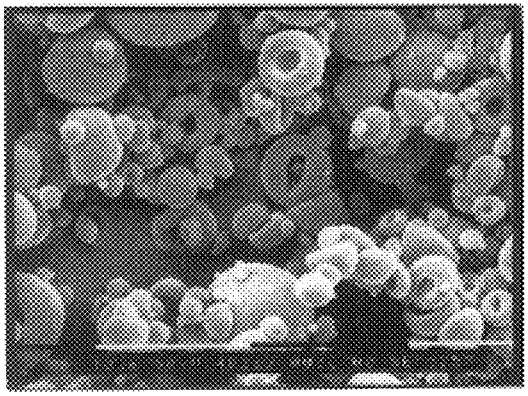
*FIG._8E*
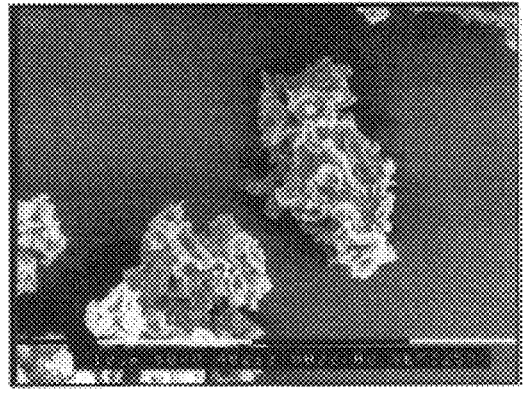
*FIG._8F*

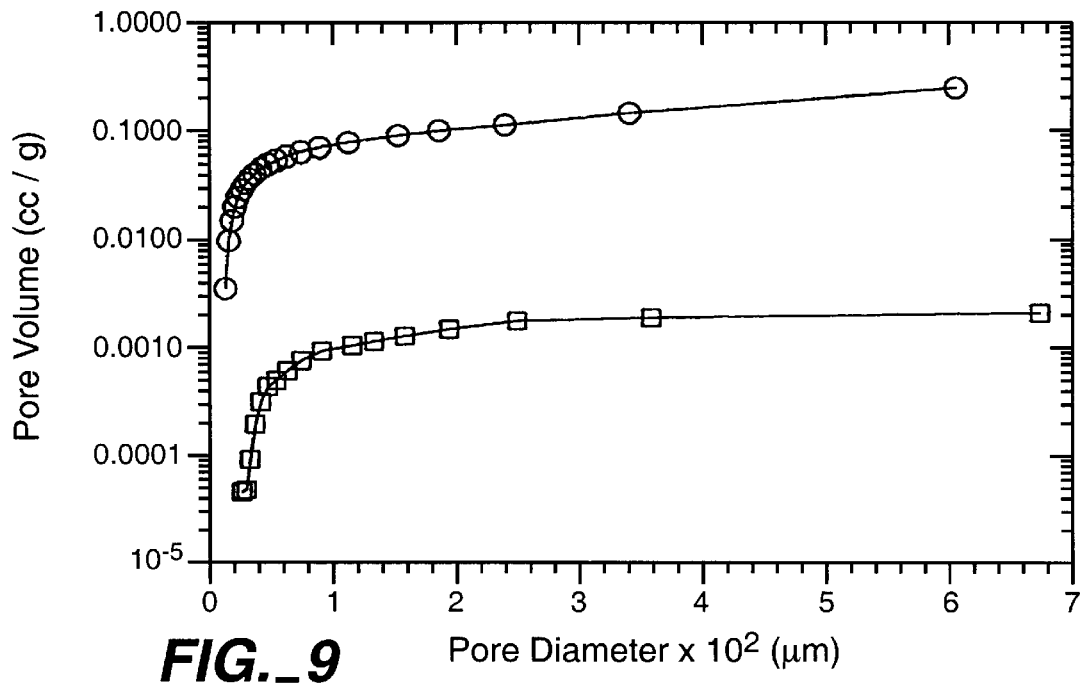
FIG._9
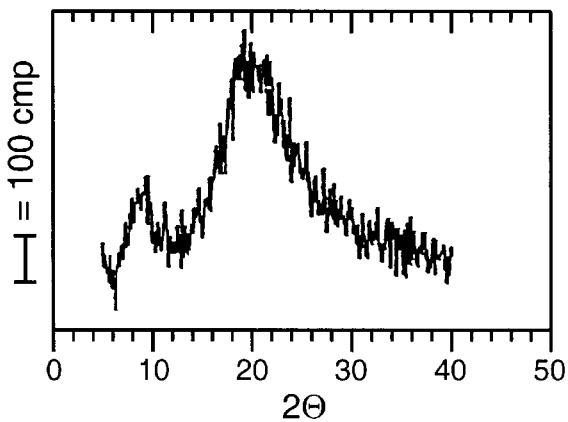
FIG._10A
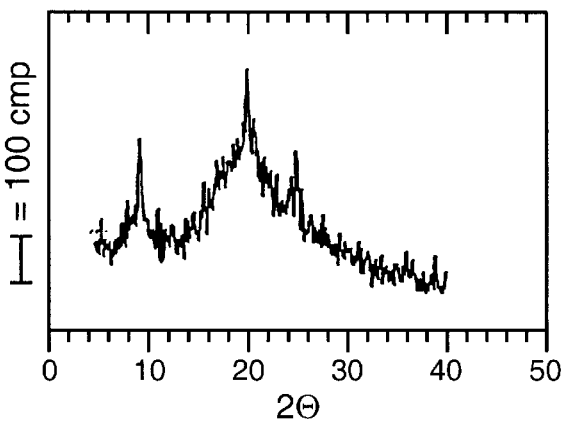
FIG._10B
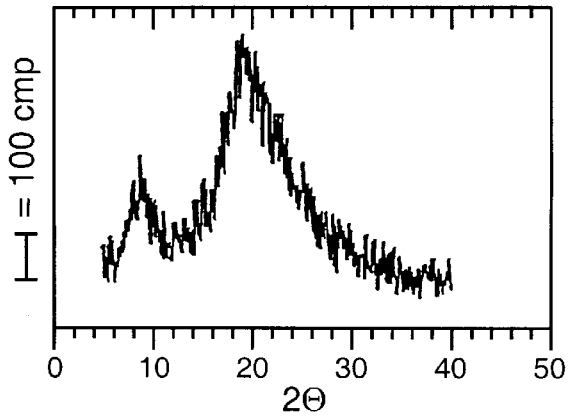
FIG._10C
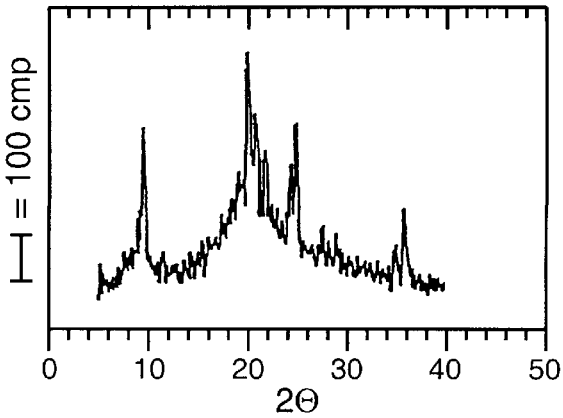
FIG._10D

METHOD OF SPRAY FREEZE DRYING PROTEINS FOR PHARMACEUTICAL ADMINISTRATION

PRIORITY INFORMATION

This is a non-provisional application claiming priority to provisional application No. 60/145,738 having an effective filing date of Apr. 29, 1998, having been converted to a Provisional Application under 35 U.S.C. § 111(b) by means of a petition filed under 37 C.F.R. 1.53(c)(2) from U.S. Ser. No. 09/069,641, filed Apr. 29, 1998, the entire disclosure of which is hereby incorporated by reference and to which application priority is claimed under 35 USC §119(e).

FIELD OF THE INVENTION

The present invention is directed to spray freeze drying of proteins for pharmaceutical administration.

BACKGROUND OF THE INVENTION

Inhalation therapy involves the administration of a drug in an aerosol from to the respiratory tract. Aerosol delivery is based on the concept that delivery to the deep lung regions (alveoli), which account of 95% of lung epithelia, can significantly enhance the transport of the protein through the epithelial membrane if the molecule is bioavailable.

Two general types of aerosols are employed: liquid particles and solid particles. The liquid aerosols are generated by nebulizing solutions of the drug. Solid particles are either in the form of a powder suspended in a propellant which is administered from a metered dose inhaler or simply as a powder that is administered from a dry powder inhaler. In the case of polypeptide drugs, solid particle aerosols are typically made by lyophilizing (also known as freeze-drying) the drug from solution and then milling or grinding the lyophilized drug to the desired particle size distribution for pulmonary administration.

Recently, the possibility of using spray-drying to formulate aerosol powders of therapeutic proteins has been discussed. Spray drying is a dehydration process that utilizes heat from a hot gas stream (usually air) to evaporate dispersed droplets created by atomization of a continuous liquid feed. Using these methods, products can be dried within a few seconds into fine particles, and this general process has been used for decades to prepare dry pigments and dairy powders. As applied to specific therapeutic proteins, however, thermal denaturation and structural alterations are a concern. This is generally attributed to the loss of hydration water molecules required to form hydrogen bonds to stabilizes the secondary structure; generally spray-drying is done with excipients such as carbohydrates that can act as water-replacing agents.

There are several reports of spray drying therapeutic proteins for pulmonary delivery. Maa et al. report on the use of polysorbate-20 surfactant to form stable, rhGH formulations. *J. Pharm. Sci.* 87(2):152 (1998). See also Mumenthaler et al., *Pharm. Res.* 11(1):12 (1994); Chan et al., *Pharm. Res.* 14(2):431 (1997), and WO 97/41833, which discusses the spray-drying of biological macromolecules.

In addition, Gombotz et al. discuss a system for spraying polymers dissolved in solvents into freezing liquids and then extracting the solvents, to form hardened microspheres. The polymers also can contain active agents such as proteins, peptides, nucleic acids, etc., to form microspheres suitable for controlled release of the active agents. See U.S. Pat. No. 5,019,400 and WO 90/13285. Also, there are reports of forming particulate proteins using spraying into super critical fluids; see Yeo et al., *Biotechnology and Bioengineering* 41:341 (1993) and Winters et al., *J. Pharm. Sci.* 85(6):586 (1996).

Considerable attention has been given to the design of therapeutic aerosol inhalers to improve the efficiencies of inhalation therapies. This includes exploration of the aerosol's surface texture, in an attempt to avoid particle aggregation, a phenomenon that considerably diminishes the efficacy of inhalation therapies. However, there has been little focus on the possibility of using large particle sizes (greater than 5 µm), despite the fact that intra particle adhesion diminishes with increasing particle size. This is so because particles of greater than 5 µm are known to deposit excessively in the upper airways to the exclusion of the alveolar regions of the deep lung.

Thus, dry powder aerosols for inhalation therapies are produced with mean diameters of less than 5 µm. There has been work done using polyester graft copolymers that are have mean diameters from 5 to 30 µm but are aerodynamically light; see WO 97/44013.

Accordingly, there is a need to provide improved compositions for the aerosol delivery of therapeutic proteins in a form that shows high dispersibility and good respirability properties.

SUMMARY OF THE INVENTION

In accordance with the objects outlined above, the present invention provides spray freeze dried dry powder therapeutic protein compositions for pulmonary administration comprising particles of a protein of an average size 6–8 µm. The compositions may be substantially free of an excipient.

In an additional aspect, the present invention provides methods of preparing a dry powder composition comprising spray freeze-drying an aqueous mixture of a protein under conditions to provide a respirable dry powder. Preferably, the method comprises atomizing a liquid formulation comprising a therapeutic protein into a cold fluid to prepare frozen droplets. The water is removed from the droplets to form powder particles and the particles are recovered. The method may additionally comprise an annealing step, wherein the temperature of the frozen droplets is raised prior to the removal of the water.

In a further aspect, the invention provides methods for aerosolizing a spray freeze dried dry powder therapeutic protein composition comprising dispersing an amount of the dry powder in a gas stream to form an aerosol. The aerosol may be captured in a chamber suitable for subsequent inhalation by a patient.

In an additional aspect, the invention provides methods of administering a therapeutically effective dose of a therapeutic protein to a patient comprising administering to the alveolar regions of the lungs of the patient a spray freeze dried therapeutic protein dry powder composition.

In an additional aspect, the invention provides methods of treating a disorder associated with the therapeutic protein comprising administering to the alveolar regions of the lungs of a patient a dry powder composition of the invention.

In a further aspect, the invention provides unit dosage receptacles and dry powder inhalers comprising a therapeutically effective amount of the dry powder compositions of the invention.

BRIEF DESCRIPTION OF THE DRAWINGS

FIG. 1 depicts a schematic representation of the experimental set-up for spray freeze drying.

FIG. 2 depicts a schematic representation of a multiple-stage liquid impinger system.

FIGS. 3A and 3B depict a schematic representation of the Anderson cascade impactor system. (A) the complete system and (b) the air flow within each plate.

FIGS. 4A, 4B, 4C and 4D are SEMs for four powders. (A) is spray freeze dried pure rhDNase; (B) is spray dried pure rhDNase.(C) is spray-freezed dried anti-IgE antibody containing 5 mM histidine. (D) is spray dried anti-IgE antibody.

FIGS. 5A and 5B show the comparison of powder dispersion by liquid impingement between spray-dried and spray freeze-dried powders for pure rhDNase (A) and anti-IgE antibody (B).

FIGS. 6A, 6B and 6C show the comparison between aerodynamic particle size distribution for the aerosolized powder (squares) and the fully dispersed raw powder (circles) based on liquid impingement data for the spray-dried anti-IgE antibody powder (A) and the spray freeze-dried anti-IgE antibody powder (B). The mass median aerodynamic diameter for the aerosolized spray-dried (squares and spray freeze-dried (circles) anti-IgE antibody powders is presented in (C).

FIGS. 7A, 7B, 7C and 7D show SEMs for particles of 80/10/10 E25/mannitol/glycine collected in the Anderson cascade impactor from Stages 2 (4.7–5.8 $\mu$m) for the spray-dried powder (a) and for the spray freeze-dried powder (b) and from Stage 5 for the spray-dried powder (c) and for the spray freeze-dried powder (d).

FIGS. 8A, 8B, 8C, 8D, 8E, and 8F show SEMs for the spray-dried powder (a) and the spray freeze-dried powder (b) of 50/50 rhDNase/mannitol, for the spray-dried powder (c) and for the spray freeze-dried powder (d) of 40/60 rhDNase/trehalose,and for the spray-dried powder (e) and for the spray freeze-dried powder (f) of 60/20/20 E25/mannitol/trehalose.

FIG. 9 shows the cumulative pore volume vs. pore size for rhMAb powders prepared by spray freeze drying (circles) and freeze drying (squares).

FIGS. 10A, 10B, 10C and 10D depict the X-ray powder diffraction analysis on powders of 80:20 rhMAb:mannitol prepared by (a) freeze drying and (b) spray freeze drying, and powders of 60:40 rhMAb:mannitol containing 50 mM sodium phosphate prepared by (c) freeze drying and (d) spray freeze drying.

FIG. 11 shows the effect of the freezing rate, (droplet diameter)⁻, on the (empty circles) surface area of the SFD powder (60:40 rhMAb:trehalose)(Y1 axis) and on (filled circles) protein aggregation (Y2 axis).

DETAILED DESCRIPTION OF THE INVENTION

The present invention is directed to methods and compositions comprising spray freeze-dried formulations of therapeutic proteins, that show good dispersibility and respirable properties, as well as good stability. In a further aspect, the present invention is directed to the surprising discovery that stable dry powder formulations of therapeutic proteins such as IGF-I can be prepared without the use of excipients, i.e. protectants. Generally, as is known in the art, formulations of proteinaceous drugs that have been frozen (i.e. such as is done in lyophilization) require the use of excipients such as carbohydrates, polypeptides, etc., both for stability during the freezing process and for shelf stability. However, surprisingly, some proteins are able to form stable and highly useful dry powders for aerosol pulmonary administration in the absence of such excipients.

The success of a dry powder inhalation product is based on the ease of powder dispersibility, which is mainly determined by the efficiency of inhalation devices and by the physical properties of the powder. Many physical characteristics affect the dispersibility of the powder, including the nature of the material, particle size/distribution, particle shape/morphology, and moisture content. All these properties affect the interparticle (cohesion) forces and/or the particle-surface (adhesion) forces. Increased interparticle cohesion reduces powder segregation, resulting in physically larger particles which are difficult to be inhaled to the deep lung. Increased particle surface adhesion decreases powder flowability and increases powder retention on all contact surfaces. However, even when particles are physically small enough (<5 $\mu$m), they are likely to be deposited on the wall of the respiratory track on their way down to the alveoli regions of the lungs because inertial deposition is often the most dominating deposition mechanism. Particles with sufficient inertia can easily escape from the streamlines of air flow and deposit on the airway. Therefore, the present invention is directed to particles that have lower inertia but retain the ability to reach the deep lung.

A particle (diameter $D_s$ and density $\rho_s$) moving in air (density $\rho_a$ and viscosity $\mu$) reaches a terminal velocity ($v_t$) as the result of force balance between gravity, buoyancy force, and the drag force by the air fluid in the opposing direction. This is generally described in Equation 1:

$$(1/6)\pi D_s^3 r_s g = (1/6)\pi D_s^3 r_a g + 3\pi\mu v_t D_s \qquad \text{Equation 1}$$

(gravity)     (buoyancy)     (drag force)

Since $\rho_a \ll \rho_s$, eq.(1) can be rewritten into Equation 2 by neglecting the buoyancy force:

$$D_s^2 \rho_s = 18(\mu/g) v_t \qquad \text{Equation 2}$$

A particle of unit density with an aerodynamic diameter ($D_a$) moves with the same terminal velocity as the particle in Equation, i.e. $D^a = D_s \rho_s^{0.5}$. The significance of aerodynamic particle size lies in combining the influence of particle's physical size and inertia. Assuming a light (low density) particle having the same physical size ($D_s$) as a heavy (high density) particle, the light particle will have a smaller aerodynamic size than the heavy particle; therefore, light particles are likely to travel with air streamlines and reach in the deep lung for effective deposition.

Inertial impactation and gravitational settling of aerosols are the predominant deposition mechanisms. The importance of both deposition mechanisms increases in proportion to the mass of the aerosols and not to the volume (i.e. size). Since the site of aerosol deposition in the lungs is determined by the mass of the aerosol, diminishing the density of the particle may permit the delivery of larger particle sizes into the deep lungs. In addition, larger particles may show decreased or slower phagocytosis in the lung thus allowing better delivery of the drug; see Edwards et al., *Science* 276:1868 (1997), hereby expressly incorporated by reference.

Changes in aerodynamic size for particles of the same composition and shape can be made by changing particle density, for example, from a solid sphere to a porous ball. As shown herein, this may be accomplished by preparing the particles by a spray freeze drying process, wherein the formulation comprising the drug is sprayed into either a gas or a liquid at a temperature below the freezing point of the formulation to form small, generally spherical frozen particles, that are collected and then dried, such that the solvent is removed, forming very porous particles, that are larger than is traditionally thought desirable, yet are very light.

Thus, the present invention provides spray freeze dried dry powder therapeutic protein compositions. By "spray freeze dried" herein is meant that the composition is prepared by spray freeze drying. Spray freeze drying is a process conceptually similar to spray drying, in that a homogeneous aqueous mixture of a therapeutic protein, termed herein the "pre-spray freeze dry formulation", is introduced via a nozzle (e.g. a two-fluid nozzle), spinning disk or an equivalent device into a cold fluid to atomize the solution to form fine droplets. The aqueous solution is preferably a solution, although suspensions, slurries or the like may be used as long as it is homogeneous to ensure uniform distribution of the protein in the solution and ultimately in the powdered composition. The cold fluid, either a liquid or a gas, is at a temperature below the freezing point of the aqueous solvent of the pre-spray freeze dry formulation. Spraying the formulation into the cold fluid results in the rapid freezing of the atomized droplets to form particles. The particles are collected, and then the solvent is removed, generally through sublimation (lyophilization)in a vacuum. As discussed below, the particles may be annealed (i.e. the temperature raised) prior to drying. This produces a fine dry powder having particles of a specified size and characteristics, as are more fully discussed below. Suitable spray freeze drying methodologies are also described below.

The term "powder" means a composition that consists of finely dispersed solid particles that are relatively free flowing and capable of being readily dispersed in an inhalation device and subsequently inhaled by a patient so that the particles can reach the alveoli of the lung. Thus, the powder is "respirable" and suitable for pulmonary delivery.

The term "dispersibility" means the degree to which a powder composition can be dispersed (i.e. suspended) in a current of air so that the dispersed particles can be respired or inhaled into the lungs of a subject. Thus, a powder that is only 20% dispersible means that only 20% of the mass of the particles can be suspended for inhalation into the lungs.

The spray freeze dried powders of the invention may be characterized on the basis of a number of parameters, including, but not limited to, the average particle size, the range of particle sizes, the fine powder fraction (FPF), the average particle density, and the mass median aerodynamic diameter (MMAD).

In a preferred embodiment, the spray freeze dried powders of the invention are characterized on the basis of their average particle size. Preferably the average particle size ranges from about 5 $\mu$m to about 30 $\mu$m, with from about 5 to about 20 $\mu$m being more preferred and from about 5 to about 10 $\mu$m being especially preferred. A preferred average particle size is 6–8 $\mu$m. The average particle size of the powder can be measured as mass mean diameter (MMF) by convention techniques.

In a preferred embodiment, the powders of the invention are characterized on the basis of their fine particle fraction (FPF). The FPF is a measure of the aerosol performance of a powder, with the higher the fraction, the better. The FPF is defined as powder with an aerodynamic mass median diameter of less than 6.8 $\mu$m as determined using a multiple-stage liquid impinger with a glass throat (MLSI, Astra, Copley Instrument, Nottingham, UK) through a dry powder inhaler (Dryhalter™, Dura Pharmaceuticals); see FIG. 5. Accordingly, the IGF-I spray-dried powders of the invention preferably have a FPF of at least about 10%, with at least about 20% being preferred and at least about 30% being especially preferred, with some systems enabling very high FPFs, in the order of 40 to 50%.

Similarly, the powders of the invention may be characterized on the basis of the density of the particles comprising the compositions of the invention. In a preferred embodiment, the particles have a tap density of less than about 0.8 g/cm$^3$, with tap densities of less than about 0.4 g/cm$^3$ being preferred and less than about 0.1 g/cm$^3$ being especially preferred. The tap density of particles of a dry powder may be measured using a GeoPyc™ (Micrometrics Instruments Corp). Tap density is a standard measure of the envelope mass density. The envelope mass density of an isotropic particle is defined as the mass of the particle divided by the minimum sphere envelope volume within which it can be enclosed.

In a preferred embodiment, the aerodynamic particle size of the spray freeze dried powders of the invention is characterized as is generally outlined in the examples. Similarly, the mass median aerodynamic diameter (MMAD) of the particles may be evaluated, using techniques well known in the art.

In addition to the above characteristics, the particles can be characterized on the basis of their general morphology as well. In general, particles made by the processes of the invention are generally spherical and porous.

The term "dry" means that the composition has a moisture content such that the particles are readily dispersible in an inhalation device to form an aerosol. This moisture content is generally below about 15% by weight water, with less than about 10% being preferred and less than about 5% being particularly preferred.

The spray freeze dried powders of the invention comprise therapeutic proteins. By "proteins" herein meant proteins, polypeptides and peptides. As will be appreciated by those in the art, a wide variety of therapeutic proteins may be processed using the methods of the invention. In general, suitable therapeutic proteins include, but are not limited to, growth factors, cytokines, antigens, antibodies, interleukins, lymphokines, interferons, enzymes, etc., including, but not limited to, anti-IgE antibodies, tissue plasminogen activator (tPA), calcitonin, erythropoeitin (EPO), factor IX, granulocyte colony stimulating factor (G-CSF), granulocyte macrophage colony stimulating factor (GM-CSF), growth hormone (particularly human growth hormone), heparin (including low molecular weight heparin), insulin, insulin-like growth factors I (IGF-I) and II (IGF-II), interleukins, interferons $\alpha$, $\beta$ and $\gamma$, luteininzing hormone releasing hormone, somatostatin and analogs, vasopressin and analogs, follicle stimulating hormone, amylin, ciliary neurotrophic factor, growth hormone releasing factor, insulinotropin, macrophage colony stimulating factor(M-CSF), nerve growth factor, parathryoidhormone, $\alpha$-1 antitrypsin, anti-RSV antibody, interferons ($\alpha$, $\beta$, and $\gamma$), DNase, Her2, etc.

Particularly preferred therapeutic proteins include, but are not limited to, IGF-I, anti-IgE antibodies, human growth hormone, Dnase, tPA, IFN-$\gamma$ and $\alpha$-1 antitrypsin.

In addition, the therapeutic protein powders of the invention preferably comprise substantially bioactive proteins. That is, as is known for many dry powder formulations, some percentage of the protein in the powder can aggregate, resulting in a loss of activity. Similarly, there may be misfolded protein present, for example as a result of denaturation due to freezing, that may or may not aggregate. Accordingly, preferred embodiments provide powders that have at least about 70% active protein (i.e. the percentage of active protein to total protein present), with at least about 80% active protein being preferred, and at least about 90% active protein being especially preferred. The measurement of the total protein present will depend on the protein, and generally will be done as is known in the art, and can be done on the basis of activity assays, immunology assays, etc. The measurement of the active protein present will be dependent on the protein and will be done on suitable bioactivity assays as will be appreciated by those in the art.

In general, freeze drying is composed of two stress vectors: freezing and dehydration (Carpenter et al. *Arch. Biochem. Biophys.*, 303: 456–464 (1993), Prestrelski et al., *Arch. Biochem. Biophys.*, 303: 465–473 (1993), Crowe et al., *Cryobiology*, 27: 219–231 (1990)). However, in spray freeze drying, the individual stress event might arise due to atomization (shear stress and air-liquid interfacial stress), cold denaturation, freezing (ice-water interfacial stress and shear stress), and dehydration. A large number of studies have been devoted to understanding the effect of lyophilization on protein stability using cryoprotectants against freezing destabilization(Shikama et al. *Nature*, 190: 83–84 (1961), Chilson et al. *Fed. Proc.* 24: S55–S65 (1965), Tamiya et al., *Cryobiology*, 22: 446–456 (1985), Carpenter et al. *Cryobiology*, 25: 244–255 (1988), Nema et al. *J. Parent. Sci. Techn.*, 47: 76–83 (1993), Chang et al. *J. Pharm. Sci.*, 85: 1325–1330 (1996)), and lyoprotectants against dehydration and long-term storage destabilization (Townsend et al., *J. Parent. Sci. Technl.*, 42: 190–199 (1988), Carpenter et al., *Cryobiology*, 25: 459–470 (1988), Izutsu et al. *Int. J. Pharm.*, 71: 137–146 (1991), Izutsu et al. *Int. J. Pharm.*, 90: 187–194 (1993)). The mechanism of cryoprotectant molecules (sugars, amino acids, polyols, etc.) preferentially excluded from the surface of protein molecules has been widely used to describe the stabilization of proteins in the highly concentrated unfrozen liquid associated with ice crystallization(Crowe, et al. supra, Arakawa, et al. *Biochem.*, 21: 6536–6544 (1982), Arakawa, et al. *Biochem.*, 21: 6545–6552 (1982), Arakawa, et al. *Arch. Biochem. Biophys.*, 224: 169–177 (1983)).

However, protein denaturation at ice-water interfaces upon freezing represents another stress event during freezing (Nema et al. supra, Chang et al. supra, Hsu et al. *Pharm. Res.*, 12: 69–77 (1995), Eckhardt et al. *Pharm. Res.*, 11:1360–1364 (1991), Strambini, et al. *Biophy. J.*, 70: 971–976 (1996), Watanabe et al., *Agric. Biol. Chem.*, 52: 2517–2523 (1988). Most of these studies (Chang et al. supra, Hsu, et al. supra, Eckhardt et al., supra, Strambini, et al. supra) suggested that the rate of denaturation increases with the ice-water interfacial area and this interfacial area increases with the freezing rate. Fast freezing resulted in a larger number of ice nuclei, each of which could grow into a smaller ice crystal, thereby generating a larger specific ice-water interfacial area than a slow freezing process which produced a smaller number of larger ice crystals. Interestingly, a low-molecular weight surfactant could effectively reduce the protein's denaturation tendency at the ice-water interface (Chang et al., supra, Watanabe et al. supra) in a manner similar to that at the air-liquid interface (Maa, et al. *J. Pharm. Sci.*, 87: 152–159 (1998), Maa et al. *Biotech. Bioeng.*, 54: 503–512. (1997).). Hsu et al. supra reported a linear correlation between the amount of protein insoluble aggregates and the internal surface area of the lyophilized cake, and a linear relationship between the internal surface area and the freezing rate was also found. It appears that the fastest cooling rate was achieved by dipping a small volume (1 mL) of the protein solution in a 3-mL vial into liquid nitrogen (Nema et al, supra, Chang, et al. supra). Although the actual freezing rate was not reported, it might still take a few seconds for the whole sample volume to be frozen.

However, the present invention utilizes methods that result in extremely fast rates of freezing, due to the small droplet size and very low temperatures.

In one embodiment, the spray freeze-dried compositions of the invention may preferably contain excipients. "Excipients" or "protectants" (including cryoprotectants and lyoprotectants) generally refer to compounds or materials that are added to ensure or increase the stability of the protein during the spray-freeze dry process and afterwards, for long term stability and flowability of the powder product. Suitable excipients are generally relatively free flowing particulate solids, do not thicken or polymerize upon contact with water, are basically innocuous when inhaled by a patient and do not significantly interact with the therapeutic protein in a manner that alters its biological activity. Suitable excipients include, but are not limited to, proteins such as human and bovine serum albumin, gelatin, immunoglobulins, carbohydrates including monosaccharides (galactose, D-mannose, sorbose, etc.), disaccharides (lactose, trehalose, sucrose, etc.), cyclodextrins, and polysaccharides (raffinose, maltodextrins, dextrans, etc.); an amino acid such as monosodium glutamate, glycine, alanine, arginine or histidine, as well as hydrophobic amino acids (tryptophan, tyrosine, leucine, phenylalanine, etc.); a methylamine such as betaine; an excipient salt such as magnesium sulfate; a polyol such as trihydric or higher sugar alcohols, e.g. glycerin, erythritol, glycerol, arabitol, xylitol, sorbitol, and mannitol; propylene glycol; polyethylene glycol; Pluronics; surfactants; and combinations thereof.

Preferred excipients are trehalose, sucrose, sorbitol, and lactose.

Generally, when excipients are used, they are used in amounts ranging from about 1 to 95 wt %, with from about 1 to 50 wt % preferred, from about 10 to 50 wt % being especially preferred, and from about 10 to 20% being particularly preferred.

In a preferred embodiment, an excipient commonly used in some lyophilization processes, mannitol, is not used. As outlined in the examples, mannitol tends to crystallize, and thus loses its protective functions, in spray freeze drying.

In a preferred embodiment, the spray-freeze dried compositions of the invention do not contain substantial amounts of excipients, i.e. they are substantially free of excipients. "Substantially free" in this case generally means that the composition contains less than about 10%, with less than about 5%, and preferably less than 2–3% by weight any components other than the protein and the residual water. Generally, for the purposes of this invention, excipients do not include solvents, buffers or salts. Thus, preferred embodiments utilize spray dry formulations (prior to the addition of bulking agent, discussed below) that consist of the protein as the major component, with small amounts of buffers, salts and residual water. Generally, in this embodiment, the spray freeze dry process preferably comprises an annealing step, wherein the temperature is raised prior to drying, as is more fully outlined below.

In a preferred embodiment, the pre-spray freeze dry formulations (i.e. the solution formulation used in the spray freeze dry process) comprise the protein in water, with only negligible amounts of buffers or other compounds present. In some embodiments, the pre spray-freeze dry formulations containing little or no excipient may not be highly stable over long periods, and thus it is desirable to perform the spray-freeze drying process within a reasonable short time after producing the pre-spray freeze dry formulation. However, while the pre-spray freeze dry formulations utilizing little or no excipient may not be highly stable, the dry powders made from these formulations can, for certain proteins, be both surprisingly stable and highly dispersible, as shown in the Examples.

In a preferred embodiment, the formulations that are spray dried to form the compositions of the invention comprise the therapeutic protein in buffer, which may or may not additionally contain some salts. The pH of the buffer will generally be chosen to stabilize the protein of choice, and will be ascertainable by those in the art. Generally, this will be in the range of physiological pH, although some proteins, such as IGF-I, can be stable at a wider range of pHs, for example acidic pH. Thus, preferred pH ranges of the pre-spray freeze dry formulation are from about 1 to about 10, with from about 3 to about 8 being particularly preferred, and from about 5 to about 7 being especially preferred. As will be appreciated by those in the art, there are a large number of suitable buffers that may be used. Suitable buffers include, but are not limited to, sodium acetate, sodium citrate, sodium succinate, ammonium bicarbonate and carbonate. Generally, buffers are used at molarities from about 1 mM to about 2 M, with from about 2 mM to about 1 M being preferred, and from about 10 mM to about 0.5 M being especially preferred, and 50 to 200 mM being particularly preferred.

In a preferred embodiment, the formulations that are spray freeze dried to form the compositions of the invention comprise the therapeutic protein in solvents, which may or may not additionally contain some salts. The composition and pH of the solvent will vary with the protein, as will be appreciated by those in the art, with pharmaceutically acceptable solvents preferred. Suitable pH ranges and molarities are as outlined above for buffers. As will be appreciated by those in the art, there are a large number of suitable solvents that may be used. Suitable solvents include, but are not limited to, acids including acetic and citric acid, and alcohols such as ethanol.

In addition, when water, buffers or solvents are used, they may additionally contain salts. Generally, salts are used at molarities from about 1 mM to about 2 M, with from about 2 mM to about 1 M being preferred, and from about 10 mM to about 0.5 M being especially preferred, and 50 to 200 mM being particularly preferred. Suitable salts include, but are not limited to, NaCl.

In addition, the compositions of the invention are generally substantially free of "penetration enhancers". "Penetration enhancers" are surface active compounds that promote penetration of a drug through a mucosal membrane or lining and are generally used intranasally, intrarectally, and intravaginally. The use of penetration enhancers in the lungs however, is generally undesirable as the sensitive and fragile epithelial blood barrier in the lung can be severely affected by surface active compounds such as detergents. The dry powder compositions of the invention are readily absorbed in the lungs with the need to employ penetration enhancers.

Similarly, the compositions of the invention are generally substantially free of microsphere-forming polymers such as those described in WO 97/44013 and U.S. Pat. No. 5,019,400. That is, the powders of the invention generally comprise protein and excipient, and do not require the use of polymers for structural purposes.

Furthermore, the powders of the invention are preferably stable. "Stability" can mean one of two things, with preferred embodiments showing stability in both areas. In a preferred embodiment, stability refers to the retention of biological activity. In a preferred embodiment, stability can also refer to the retention of dispersibility of a formulation over time.

In a preferred embodiment, the dry powders of the invention retain biological activity over time, i.e. retains its physical and chemical stability and integrity upon storage. Losses in biological activity are generally due to protein aggregation, protein misfolding during processing, and protein oxidation. As will be appreciated by those in the art, there may be an initial loss of biological activity as a result of spray freeze-drying, due to the low temperatures used in the process. However, once this has occurred, further loss of activity should be minimized; that is, stability in this context is measured from the time the powder is made, rather than before the powder is made.

In a preferred embodiment, the dry powders of the invention retain dispersibility over time. Generally, this is quantified by the retention of a high FPF over time; that is, the powder minimally aggregates, cakes or clumps over time.

Stability can be measured at a selected temperature for a selected time period. As will be appreciated by those in the art, the length of time and the conditions under which a formulation should be stable will depend on a number of factors, including the amount made per batch, the storage conditions (temperature, relative humidity, etc.), the turnover of the product, etc. Generally, for rapid screening, a matrix of conditions are run. Commonly, formulations may be tested at 2–8° C., 30° C. and sometimes 40° C., for periods of 2, 4 and 24 weeks. These tests are usually done at 38% relative humidity (rh), as is outlined in the Examples. Thus, in a preferred embodiment, the powders of the invention preferably lose less than about 30% of their biological activity over 18 months, with losses of less than about 20% being preferred and less than about 10% being especially preferred. Similarly, when dispersibility is being evaluated, the powders of the invention lose less than about 50% of their FPF, with losses of less than about 30% being preferred and losses of less than about 20% being especially preferred.

In a preferred embodiment, the spray freeze dried powders of the invention are later combined with bulking agents or carriers, which are used to reduce the concentration of the therapeutic protein in the powder being delivered to a patient; that is, it may be desirable to have larger volumes of material per unit dose. Bulking agents may also be used to improve the dispersibility of the powder within a dispersion device, and/or to improve the handling characteristics of the powder. This is distinguishable from the use of bulking agents or carriers during the spray drying process. Suitable bulking agents are generally crystalline (to avoid water absorption) and include, but are not limited to, lactose and mannitol. Accordingly, bulking agents such as lactose, if added, may be added in varying ratios, with from about 99:1 rhIGF-I to bulking agent to about 1:99 being preferred, and from about 1:5 to about 5:1 being more preferred, and from about 1:10 to about 1:20 being especially preferred.

In one embodiment, the powders of the invention are formulated with other drugs. That is, combinations of therapeutic proteins may be spray freeze dried, or they may be spray freeze dried separately and combined, or one component may be spray freeze dried and the other may not. The combination of drugs will depend on the disorders for which the drugs are given, as will be appreciated by those in the art. For example, when IGF-I is the therapeutic protein, the powders of the invention may be formulated with hypoglycemic agents. The term "hypoglycemic agent" refers to compounds that are useful for regulating glucose metabolism. More preferred herein for human use are insulin and the sulfonylurea class of oral hypoglycemic agents, which cause the secretion of insulin by the pancreas. Examples include glyburide, glipizide, and gliclazide. In addition, agents that enhance insulin sensitivity or are insulin sensitizing, such as biguanides (including metformin and phenformin) and thiazolidenediones such as REZULIN™ (troglitazone) brand insulin-sensitizing agent, and other compounds that bind to the peroxisome proliferator activated receptor (PPAR) subtype PPARγ nuclear receptor, or that activate RXR, are within this definition, and also are preferred. For additional examples of PPARγ and RXR activators, see WO 97/10813 and WO 97/10819. Thus preferred embodiments utilize IGF-I co-formulation with insulin or human growth hormone.

The compositions of the invention may also comprise preservatives, detergents, surfactants, antioxidants, etc., as will be generally known in the art.

The compositions of the invention are generally made as follows. Generally, the therapeutic protein is made as will be known in the art, with recombinant methods generally preferred, as is known in the art. It may be formulated for stability as a liquid formulation in any number of formulations. Generally, for spray-freeze drying, the liquid formulations are subjected to diafiltration and ultrafiltration, as required, for buffer exchange (or removal) and/or concentration, as is known in the art. Generally, the pre-spray dry formulations comprise from about 5 mg/ml to about 75 mg/ml of the therapeutic protein, with from about 10 mg/ml or about 60 mg/ml being preferred, and from about 20 to about 60 mg/ml being especially preferred. The use of buffers and excipients, if present, are done at concentrations discussed above.

The pre-spray freeze dry formulation is then spray freeze dried as follows. The spray freeze step is done in a manner similar to spray drying, except that instead of spraying into hot air or gas, the spraying is done into a cold fluid such as liquid or gas. A preferred set up is depicted in FIG. 1.

Generally, the pre-spray freeze dry formulation is atomized as is known in the art, for example via a two-fluid nozzle or ultrasonic nozzle using filtered pressurized air, into a cold fluid.

Conventional spray drying equipment is generally used, such as Büchi, Niro Yamato, Okawara, Kakoki and the like. It is generally preferable to slightly heat the nozzle, for example by wrapping the nozzle with heating tape, to prevent the nozzle head from freezing.

The pre-spray freeze dry formulation is atomized into a cold fluid. Generally, temperatures ranging from about −200° C. to −80° C. are used, with from about −200° C. to about −100° C. being preferred, and about −200° C. being preferred (liquid nitrogen at −196° C.). The fluid may be a liquid such as liquid nitrogen or other inert fluids, or a gas such as air that is cooled. Dry ice in ethanol is not generally preferred, as the ethanol can denature some proteins. Similarly, the use of super critical fluids is also generally not preferred. In some embodiments it is preferred to stir the liquid as the atomization process occurs, although this is not required.

The atomization conditions, including atomization gas flow rate, atomization gas pressure, liquid flow rate, etc., are generally controlled to produce liquid droplets having an average diameter of from about 5 to about 30 μm, with droplets of average size 10 μm being preferred. Conventional spray drying equipment is generally used, such as Büchi, Niro Yamato, Okawara, Kakoki and the like.

Once the frozen droplets are produced, they are dried, that is, the frozen water is removed, leaving the protein, any excipients, and residual buffers, solvents or salts. This is may be done in a variety of ways, as is known in the art for lyophilization. That is, techniques that can be used for traditional lyophilization (i.e. freezing as a cake rather than as droplets) can be used herein. Generally, and preferably, a vacuum is applied. In one embodiment, the vacuum is applied at about the same temperature as freezing occurred. However, as shown in the examples, it may be possible to relieve some of the freezing stress on the protein by raising the temperature of the frozen particles slightly prior to or during the application of the vacuum. This process, termed "annealing", has been shown to reduce protein inactivation, as outlined in the Examples. This may be done as one or more steps; that is, the temperature can be increased one or more times either before or during the drying step of the vacuum. Preferred embodiments utilize at least two thermal increases.

Accordingly, in a preferred embodiment, the vacuum step is done at temperatures above the temperature used for freezing but below the freezing point. Preferred annealing temperatures include an initial increase such that the vacuum is applied when the particles are at a temperature of from about −10° C. to about −80° C., with from about −30° C. to about −60° C. being preferred, and about −50° C. being most preferred. Optionally and preferably a second increase in temperature is done upon the introduction of the vacuum, with the majority of the lyophilization occurring at a temperature of from about −10° C. to about −50° C., with from about −20° C. to about −40° C. being preferred, and about −25° C. being most preferred.

Thus, in a preferred embodiment, the particles are incubated for a period of time, generally sufficient time for thermal equilibrium to be reached (i.e. depending on the sample size and efficiency of heat exchange one to several hours is generally sufficient), prior to the application of the vacuum. The vacuum is applied and another annealing step is done.

The particles are lyophilized for a period of time sufficient to remove the majority of the water in the particles. The actual period of time will depend on the temperature, the strength of the vacuum, the size of the sample, etc. Generally, the particles are lyophilized to a dryness of about 1 to 10% remaining water, and from about 1 to about 5% being preferred.

In a preferred embodiment, a secondary drying step under lyophilization is done. Secondary drying in this context means that additional water is removed. This is generally done at temperatures from about 0° C. to about 50° C., with from about 10° C. to about 25° C. being preferred and about 20° C. being the most preferred.

The powders are collected using conventional techniques, and bulking agents, if desirable, are added.

Once made, the powders of the invention are capable of being readily dispersed by an inhalation device and subsequently inhaled by a patient so that the particles are able to penetrate into the alveolar regions of the lungs of the patient. Thus, the powders of the invention are formulated into unit dosages comprising therapeutically effective amounts of therapeutic proteins, and used to deliver therapeutic proteins to a patient, for example for the treatment of any number of disorders that are associated with the particular therapeutic protein.

The therapeutic protein to be used in the therapy will be formulated and dosed in a fashion consistent with good medical practice, taking into account, for example, the type of disorder being treated, the clinical condition of the individual patient (especially the side effects of treatment with the protein), whether the protein is administered for preventative or therapeutic purposes, the concentration of the protein in the dosage, previous therapy, the patient's clinical history and response to the protein, the method of administration, the scheduling of administration, the discretion of the attending physician, and other factors known to practitioners. The "effective amount" or "therapeutically effective amount" of the protein for purposes herein will depend on the identity of the protein and is thus determined by such considerations and is an amount that increases and maintains the relevant, favorable biological response of the mammal. The protein is suitably administered to the patient at one time or over a series of treatments and may be administered to the patient at any time from diagnosis onwards.

Thus, the present invention provides spray-dried dry powder formulations of therapeutic proteins in unit dosages. A "unit dosage" as discussed herein means a unit dosage receptacle containing a therapeutically effective amount of a spray freeze dried therapeutic protein. The dosage receptacle is one that fits within a suitable inhalation device to allow for the aerosolization of the powder formulation by dispersion into a gas stream to form an aerosol. These can be capsules, foil pouches, vials, etc. The container may be formed from any number of different materials, including plastic, glass, foil, etc. The container generally holds the spray-dried powder, and includes directions for use. The unit dosage containers may be associated with inhalers that will deliver the powder to the patient. These inhalers may optionally have chambers into which the powder is dispersed, suitable for inhalation by a patient.

Additionally, the powder compositions of the invention may be further formulated in other ways, for example, in the preparation of sustained release compositions, for example for implants, patches, etc. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (Sidman et al., *Biopolymers*, 22, 547–556 [1983]), poly(2-hydroxyethyl methacrylate) (Langer et al., *J. Biomed. Mater. Res.*, 15: 167–277 (1981), and Langer, *Chem. Tech.*, 12: 98–105 [1982]), ethylene vinyl acetate (Langer et al., supra) or poly-D-(-)-3-hydroxybutyric acid (EP 133,988). The spray-freeze dried powder can also be used to prepare a PROLEASE™ formulation of the protein. Sustained-release compositions also include liposomally entrapped proteins. Liposomes containing proteins are prepared by methods known per se: DE 3,218,121; Epstein et al., *Proc. Natl. Acad. Sci. U.S.A.*, 82: 3688–3692 (1985); Hwang et al., *Proc. Natl. Acad. Sci. U.S.A.*, 77: 4030–4034 (1980); EP 52,322; EP 36,676; EP 88,046; EP 143,949; EP 142,641; Japanese Pat. Appln. 83–118008; U.S. Pat. Nos. 4,485,045 and 4,544,545; and EP 102,324. Ordinarily, the liposomes are of the small (from or about 200 to 800 Angstroms) unilamellar type in which the lipid content is greater than about 30 mol. percent cholesterol, the selected proportion being adjusted for the optimal therapy.

In a preferred embodiment, the spray freeze dried powders of the invention are not inhaled; rather they are injected as dry powders, using relatively new injection devices and methodologies for injecting powders. In this embodiment, the dispersibility and respirability of the powder is not important, and the particle size may be larger, for example in the 20 to 70 $\mu$m range.

It should also be noted that the powder compositions of the invention may be reconstituted for injection as well. That is, the powders of the invention show good stability, and thus in some embodiments they can be reconstituted into liquid form using a diluent and used in non-pulmonary routes of administration, for example, via injection (subcutaneously, intravenously, etc.). In this embodiment, any number of known diluents can be used, as will be appreciated by those in the art, including physiological saline, other buffers, salts, etc. Alternatively, it is also possible to reconstitute the powder and use it to form liquid aerosols for pulmonary delivery.

The compositions of the invention are useful to deliver therapeutic proteins to a patient, for example for the treatment of disorders associated with the protein.

In a preferred embodiment, the therapeutic protein is IGF-I or variants thereof, and the disorder is an IGF-I associated disorder. By "IGF-I associated disorder" or "disease state responsive to treatment by IGF-I" or "a disorder requiring treatment with IGF-I" is any condition that would benefit from treatment with IGF-I, including but not limited to, for example, diabetes, lung diseases, hyperglycemic disorders as set forth below, renal disorders, such as acute and chronic renal insufficiency, end-stage chronic renal failure, glomerulonephritis, interstitial nephritis, pyelonephritis, glomerulosclerosis, e.g., Kimmelstiel-Wilson in diabetic patients and kidney failure after kidney transplantation, obesity, GH-insufficiency, Turner's syndrome, Laron's syndrome, short stature, undesirable symptoms associated with aging such as obesity and increased fat mass-to-lean ratios, immunological disorders such as immunodeficiencies including decreased CD4 counts and decreased immune tolerance or chemotherapy-induced tissue damage, bone marrow transplantation, diseases or insufficiencies of cardiac structure or function such as heart disfunctions and congestive heart failure, neuronal, neurological, or neuromuscular disorders, e.g., peripheral neuropathy, multiple sclerosis, muscular dystrophy, or myotonic dystrophy, and catabolic states associated with wasting caused by any condition, including, e.g., trauma or wounding or infection such as with a bacterium or human virus such as HIV, wounds, skin disorders, gut structure and function that need restoration, and so forth. The disorder being treated may be a combination of two or more of the above disorders. The preferred disorders targeted for treatment herein are hyperglycemic disorders, including diabetes, obesity, heart disfunctions, kidney disorders, neurological disorders, whole body growth disorders, and immunological disorders. As used herein, the term "hyperglycemic disorders" refers to all forms of diabetes and disorders resulting from insulin resistance, such as Type I and Type II diabetes, as well as severe insulin resistance, hyperinsulinemia, and hyperlipidemia, e.g., obese subjects, and insulin-resistant diabetes, such as Mendenhall's Syndrome, Werner Syndrome, leprechaunism, lipoatrophic diabetes, and other lipoatrophies. The preferred hyperglycemic disorder is diabetes, especially Type I and Type II diabetes. "Diabetes" itself refers to a progressive disease of carbohydrate metabolism involving inadequate production or utilization of insulin and is characterized by hyperglycemia and glycosuria.

As used herein, the term "treating" refers to both therapeutic treatment and prophylactic or preventative measures. Those in need of treatment include those already with the disorder as well as those prone to having the disorder or diagnosed with the disorder or those in which the disorder is to be prevented. Consecutive treatment or administration refers to treatment on at least a daily basis without interruption in treatment by one or more days. Intermittent treatment or administration, or treatment or administration in an intermittent fashion, refers to treatment that is not consecutive, but rather cyclic in nature. The treatment regime herein can be consecutive or intermittent or any other suitable mode. In addition, the term "treating" includes management of a particular disorder, as in the management of hyperglycemic disorders and obesity.

In a preferred embodiment, the therapeutic protein is DNase or variants thereof. As is known in the art, DNase I and II have been used to reduce the viscoelasticity of pulmonary secretions (including mucus) in such diseases as pneumonia and cystic fibrosis, thereby aiding in the clearing of airways. Mucus also contributes to the mobidity of chronic bronchitis, asthmatic bronchitis, bronchiectasis, emphysema, acute and chronic sinusitis, and even the common cold. DNase is effective by hydrolyzing the high molecular weight DNA that is present in the secretions.

In a preferred embodiment, the therapeutic protein is an anti-IgE antibody, useful in the modulation of IgE associated disorders. IgE is a member of the immunoglobulin family that mediates allergic responses such as asthma, food allergies, type 1 hypersensitivity (anaphylactic hypersensitivity) and sinus inflammation.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

EXAMPLES

Example 1

Comparison of Spray Drying and Spray Freeze Drying of rhMab and rhDNase

Recombinant-derived humanized anti-IgE monoclonal antibody (rhMAb; also termed "E25" herein; 146.54 kDa molecular weight) and recombinant human deoxyribonuclease (rhDNase) (32.74 kDa) were produced at Genentech, Inc., as glycoproteins produced in Chinese hamster ovary cell lines. Both recombinant proteins contained carbohydrates. Excipient-free anti-IgE antibody and rhDNase solutions were prepared by ultrafiltration(UF) and diafiltration (DF) into a concentration of 50 g/L, and then appropriate amounts of a sugar excipient were added to prepare a desired formulation. All protein solutions were filtered with a 0.22 μm filter before use.

Excipients used in study include mannitol, trehalose, sucrose, histidine and glycine. They were obtained from Sigma and were used as supplied.

Spray Drying: Spray drying was performed using a Model 190 Buchi mini spray dryer (Brinkmann). Using compressed air from an in-house supply (~80 psi), a two-fluid nozzle (0.5 mm) atomized the protein solution. The air was filtered through a 0.22 μm Milidisk filter (Millipore) before entering the nozzle, and the flow rate was controlled by a variable area flow meter (Cole Parmer, 150 mm). A peristaltic pump (1–100 rpm, Masterflex, Cole Parmer) pumped liquid protein feed to the nozzle using silicone tubing (3 mm ID). Cooling water was circulated through a jacket around the nozzle. Some modifications were made on the original design for a scale-up operation, which included the replacement of the bag-filter unit with a vacuum cleaning unit (Model 005, VAC-U-MAX, Belleville, N.J.) and relocation of the aspirator to the drying air input. The standard operating condition was: $T_{inlet}$ (inlet air temperature) of 105° C., $Q_{DA}$ (drying air flow rate) of 1000 L/min, $Q_{AA}$ (atomizing air flow rate) of 1050 L/hr, and $Q_{LF}$ (liquid feed rate) of 15 mL/min. This condition resulted in an $T_{outlet}$ (outlet air temperature) of 50–55° C.

Spray Freeze Drying: The schematic representation of the experimental set-up is shown in FIG. 1. A two-fluid nozzle (the same nozzle used in spray drying) or an ultrasonic nozzle (Soniteck) was used for atomization. When the two-fluid nozzle was used, warm water (45° C.) was circulated to keep the liquid from freezing in the nozzle. A 3-L two-neck, round-bottom flask was filled with liquid nitrogen and was submerged in a container also containing liquid $N_2$. The liquid $N_2$ in the flask was agitated using a magnetic stirrer bar. The nozzle was pointed into the flask in the central neck which was wrapped with a heating tape to avoid nozzle head freezing. The protein liquid was atomized using an atomizing air flow rate of 1050 L/hr. Sprayed droplets froze upon contacting liquid $N_2$ The liquid feed rate was 15 mL/min for air atomization and 5 mL/min for ultrasonic atomization. After spraying, the whole content in the flask was poured into a metal tray and placed in a lyophilizer (GT20) which had been pre-chilled to −50° C. After a hold period of one hour at −50° C., vacuum was applied to the chamber. The shelf temperature was increased to −25° C. over a two-hour period and held for 40 hours. During secondary drying, the shelf temperature was increased to 20° C. over a four-hour period and was held for another 20 hours.

Protein and Powder Characterizations

Native Size-Exclusion Chromatography (SEC-HPLC)

Soluble aggregation of rhMAb was determined by SEC-HPLC on a Bio-Select SEC 250-5 column (Bio-Rad). The column was equilibrated and run in phosphate buffered saline at a flow rate of 0.5 mL/min using a 1090L HPLC (Hewlett Packard) system. Molecular weight standards (Bio-Rad) consisting of thyroglobulin (670 kd), gamma-globulin (158 kd), ovalbumin (44 kd), and cyanocobalamin (1.35 kd) were used to calibrate the column. The sample load was 25 μg and protein was detected by monitoring the UV adsorption at 214 nm.

Soluble aggregation of rhDNase was determined by SEC-HPLC on a silica-based Tosoh TSK2000SWXL column (7.8-mm I.D.×30-cm L; particle size, 5 μm). The column was equilibrated and run in 5 mM Hepes, 150 mM NaCl and 1 mM $CaCl_2$ at pH 7.0 at a flow rate of 1 mL/min using a 1090L HPLC system. The column load was 100 μg and protein was detected by monitoring the UV absorption at 280 nm.

Scanning Electron Microscopy (SEM): Surface morphology of coated powder was examined using a Philip SEM system (Model 525M). Powder samples were mounted to a sample stub, and coated under a high vacuum (<0.05 mTorr) with a layer of 10 nm gold-platinum. All samples were scanned at a voltage of 4.0 kV and their photographs were taken at two magnifications, 4,000 and 15,000.

Moisture Content Moisture content of the protein powder was measured using a thermogravimetric analyzer (TGA 7, Perkin-Elmer) linked to a data station (Model 7700, Perkin Elmer). Samples (~5 mg) were loaded in aluminum pans and heated at 4° C./min under 30 mL/min $N_2$ gas purge. The moisture content was based on the loss in weight between room temperature and 150° C.

Particle Size Analysis a Malvern laser defraction analyzer (Mastersizer-X) measured the particle size distribution of the spray-dried powder in a liquid suspension. This devices uses the diffraction pattern produced by the presence of particles or droplets in a monochromatic coherent laser beam to deduce their size distribution. The instrument determines their diffraction pattern using an annular detector with 32 concentric detector rings and then inverts the diffraction pattern using a light scattering theory based on a model independence analysis. The diffraction data was inverted into the particle size distribution assuming a relative refractive index of 1.33 and zero optical absorption. Several milligrams of powder were suspended in 5–10 mL of isopropyl alcohol containing a drop of 1% v/v polysorbate-20. Each suspension was sonicated for about one minute before being loaded into a stirred sample cell. During analysis laser passed perpendicularly through the sample cell and then through a lens with a focal length of 100 nm. Intensity of the scattered light was measured at different angles to calculate the volume median diameter and the distribution span. Volume median diameter was the diameter at the 50% point of the entire volume distribution. The span was defined as $[D(v,90)-D(v,10)]/D(v,50)$, where $D(v,90)$, $D(v,10)$, and $D(v,50)$ were the respective diameters at 90, 10, and 50% cumulative volume.

Specific Surface Area The specific surface area ($m^2$/g) of the powder samples was determined by the multipoint Brunauer-Emmett-Teller (BET) method from the adsorption of nitrogen gas at 77° K (Nova 2200 Gas Sorption Analyzer, Quantachrome Corp.). All samples were weighed and loaded in 9 mm large pellet cells and outgased at 25° C. for 16 hr based on the gas flow method using nitrogen. For surface area analysis, a five-point BET adsorption was performed with $P/P_0$ ranging from 0.1 to 0.3. For pore size distribution, 12-point adsorption ($P/P_0$ from 0.05 to 0.99) and 25-point desorption($P/P_0$ from 0.99 to 0.01) were performed. The desorption branch was used to calculate pore diameter and pore volume based on the BJH equation (see the operating manual for the theory). This model allowed the pore size of mesopores (0.002 $\mu$m) to be accurately measured.

Preparation of Blends Before powder dispersion measurement, each powder was blended with a lactose carrier (200M, DMV) at the 10:1 (carrier:powder) weight ratio by mixing using a tumbling mixer (Turbula, Glen Mill) and sieving using a stainless steel sieve (250 $\mu$m). The blend was first mixed for 5 min and then sieved by tapping. Some clumps were gently pressed through the sieve to deagglomerate the particles. The same mixing and sieving procedures were repeated for the second time.

Powder Dispersion by Liquid Impingement The dispersibility of each powder/carrier blend was assessed using the multiple-stage liquid impinger through a dry powder inhaler (Dryhaler, Dura Corp., San Diego, Calif.) as shown in FIG. 2. All four stages were loaded with 25 mL water before experiment. Ten doses (10–20 mg each) of the blend sample were weighed out and loaded individually directly into the dose chamber of the device. The powder was dispersed at an inspiration rate of 60 L/min. The amount of protein deposited on the throat, four stages of the impinger, and the filter, as well as the amount retained in the device was assayed by measuring the UV absorbance at 280 nm using an absorptivity of 1.6 $cm^{-1}(mg/mL)^{-1}$. The percentage of the total dose collected on the third and fourth stages and on the filter, representing the particles with the aerodynamic diameter $\leq 7$ $\mu$m, was considered as the fine particle fraction.

Powder Dispersion by Cascade Impaction The Anderson cascade impactor (FIG. 3a, 8 stage 1 ACFM Non Variable Particle Size Sampler Mark II) was also used to determine the dispersibility of each powder/carrier blend through a dry powder inhaler (Dryhaler, Dura Corp.). The detailed design of a plate is also shown in FIG. 3b. The eight metal plates of the impactor were coated with a thin layer of silicone grease to prevent particles from bouncing off the plates and becoming reentrained in the air stream. A preseparator was attached to the top of the impactor to prevent large particles or aggregates from reaching the stages. The same throat piece used in liquid impingement was connected to the preseparator. Ten doses (10–20 mg each) of the blend sample were weighed out and loaded individually directly into the dose chamber of the device was dispersed at an inspiration rate of 28.3 L/min for an inhalation time of 5 sec. After each determination the powders on each plate of the impactor was collected by rinsing with deionized water. The protein concentration was assayed by measuring the UV absorbance at 280 nm using an absorptivity of 1.6 $cm^{-1}(mg/mL)^{-1}$. The amount of protein deposited in the throat piece, the preseparator, and the device was also determined. The cutoff aerodynamic size ranges for Stage 1 to Stage 8 are 9.0–10, 5.8–9.0, 4.7–5.8, 3.3–4.7, 2.1–3.3, 1.1–2.1, 0.65–1.1, and 0.43–0.65 $\mu$m, respectively. Particles collected on the filter are smaller than 0.43 $\mu$m. The percentage of the total dose collected on the third stage and lower, representing particles with the aerodynamic diameter $\leq 5.8$ $\mu$m, was considered as the fine particle fraction.

X-ray Powder Diffraction (XRD) XRD measurements were conducted using a 35 kV×15 mA Rigaku (D/max-B, CuK$_\alpha$ radiation) X-ray diffractometer at room temperature and humidity. Approximately 100 mg of powder (loaded onto the surface of a glass slide) was required for each measurement. Samples were scanned at 0.1 degrees/sec with 1 sec. count time per increment. The range scanned was from 5 to 40 degrees.

Physical characteristics and aerosol performance of SFD vs. SD powders

Table 1 summarizes the physical properties (median particle size and residual moisture) and aerosol performance (fine particle fraction) of spray-dried and spray freeze-dried powders of pure rhDNase and anti-IgE antibody. There was a significant difference between SD and SFD. During spray drying, atomized droplets (10 $\mu$m) shrank to approximately 3 $\mu$m upon water removal in hot air, and dried particles might come in different shapes depending on drying conditions and chemical formulations (Maa et al., 1997, supra). However, for SFD, atomized droplets maintained the shape and size upon immediate freezing, and subsequent freeze drying rendered dried particles porous and the physical size of the particles remained unchanged from the droplet size (~7 $\mu$m). SEMs of these powders (FIG. 4) confirm that spray-dried particles showed spherical but dimpled shapes and spray freeze-dried particles were spherical but porous. Assuming the protein solid left in the porous structure accounted for 5% of droplet volume, the particle density of the spray freeze-dried powder would be reduced to approximately one-ninths of the density of the spray-dried particle which was determined to be 1.3 g/mL. Therefore, the aerodynamic particle size, $D_a=D_s\rho_s^{0.5}$, was calculated to be 2.7 $\mu$m for the spray freeze-dried powder and 3.5 $\mu$m for the spray-dried powder.

TABLE 1

Physical and aerosol properties of spray-dried and spray freeze-dried powders of pure rhDNase and anti-IgE antibody[a].

| Formulation | Method | Moisture Content (%) | Particle Size (μm)[b] | Respirable Fraction (%)[c] |
|---|---|---|---|---|
| Pure rhDNase | Spray drying | 7.8 | 3.4(1.2) | 46 |
| | Spray freeze drying | 12.2 | 7.0(1.4) | 70 |
| anti-IgE antibody | Spray drying | 6.0 | 3.3(1.1) | 27 |
| | Spray freeze drying | 5.3 | 7.7(1.3) | 50 |

[a]Spray drying and spray freeze drying conditions were described in the Method Section.
[b]Numbers in parenthesis represent the particle size distribution (span) defined in the Method Section.
[c]Determined using liquid impingement for particles less than 7 μm.

Table 1 also shows the fine particle fraction of these four powders as determined by a multi-stage liquid impinger. Spray freeze-dried powders consistently outperformed spray-dried powders. The weight distribution of the powder deposited in each stage of the impinger is shown in FIGS. 5a & b for pure rhDNase and anti-IgE antibody. The result indicates that the increase in powder deposition in lower stages (Stages 3 & 4 and the filter) for the spray freeze-dried powders was due mainly to the decrease in powder deposition in the device and the throat, being considered an improvement on powder flowability. In addition, as far as inhalation to the deep lung, i.e. the alveoli region (<3 μm), is concerned, a significantly better dispersibility for particles of <3 μm (Stage 4 and the filter) was observed for rhDNase, 53% vs. 15%, and for anti-IgE antibody, 20% vs. 11%, justifying the use of spray freeze-dried powders for aerosol applications.

Effect of particle size on powder dispersibility Strong intra particle (between particles) and interparticle (onto the carriers) forces as well as adhesion to contacting surfaces prevented the powder from being fully dispersed. To quantify the deviation of the aerosolized powder from complete dispersion, the plot of aerodynamic diameter vs. cumulative percent undersize would be useful. Such plots for pure spray-dried and spray freeze-dried anti-IgE antibody powders are presented in FIGS. 6a & b. Complete dispersion of a powder was simulated using powder suspension in isopropanol followed by sonication and its size distribution was determined using a laser based particle size on the suspension. In both cases, the aerosolized powder showed a sharper slope, indicating a less dispersibility. However, the spray-dried and spray freeze-dried powders showed a similar dispersibility (similar slope in FIG. 6c) but their mass median aerodynamic diameters (MMAD) were 10 and 6.5 μm, respectively. These results suggest that the superior aerosol performance by the spray freeze-dried powder might be simply due to its smaller aerodynamic particle size despite its larger physical size.

Table 2 shows another piece of evidence that powder dispersibility was affected mainly by aerodynamic particle size based on spray freeze-dried powders (anti-IgE antibody:trehalose=60:40) of three different physical sizes. Using ultrasonic atomization produced a powder of the largest physical size (32 μm). Two-fluid atomization resulted in smaller particles, 19 μm and 5.9 μm corresponding to atomizing air flow rates of 600 and 1050 L/min. Physical size had a significant effect on aerosol performance with dispersibility of the powders increasing with decreasing physical size. Powders of acceptable fine particle fractions (>30%) were only available using two-fluid atomization at high atomizing air flow rates (>1000 L/hr). However, the operating condition to produce small particles (decreasing solid concentration and increasing atomizing air:liquid ratio) is not favorable to large-scale manufacturing. The optimization of the spray freeze drying process should be based on the concerns with powder's aerosol performance and manufacturing issues.

TABLE 2

The effect of particle size of spray freeze-dried powders (anti-IgE antibody:trehalose = 60/40) on aerosol performance.

| Atomization | $Q_{AA}$ (L/hr)[a] | Particle Size (μm) | Fine Particle Fraction (%)[c] |
|---|---|---|---|
| Ultrasound | None | 32 (2.4)[b] | <10 |
| Air | 600 | 19 (1.6) | 16 |
| Air | 1200 | 5.9 (1.2) | 52 |

[a]$Q_{AA}$ is the atomizing air flow rate. Spray freeze drying conditions were described in the Method Section.
[b]Numbers in parenthesis represent the particle size distribution (span) defined in the Method Section..
[c]Determined using liquid impingement for particles less than 7 μm.

Aerodynamic particle size

To confirm the concept of aerodynamic particle size, spray-dried and spray freeze-dried powders were inhaled through a cascade impactor. The size of particles collected on Stage 2 (4.7–5.8 μm) and Stage 5 (1.1–2.1 μm) was examined based on SEM (FIGS. 7a–d). For particles collected on Stage 2, spray-dried particles (FIG. 7a) were mainly <5 μm, but some spray freeze-dried particles form the same stage (FIG. 7b) had a physical size larger than 10 μm, which was larger than the cut-off aerodynamic particle diameter of 5.8 μm. For particles collected on Stage 5, spray-dried particles (FIG. 7c) were smaller than 2 μm while some spray-freeze-dried particles had a physical size in the range of 4–5 μm, which was larger than the cut-off aerodynamic particle diameter of 2.1 μm.

Formulation effect Sugar excipients were often formulated with the protein to increase protein's biochemical stability. Sugars tested in this study included trehalose, sucrose, and mannitol. Table 3 summarizes the physical size and fine particle fraction of spray-dried and spray freeze-dried powders of rhDNase and anti-IgE antibody in formulation with these three sugars.

TABLE 3

Physical size and fine particle fraction of spray-dried and spray freeze-dried powders of rhDNase and anti-IgE antibody in formulation with different sugars.

| Formulation | Method | Median particle size (μm)[a] | Fine particle fraction (%)[b] |
|---|---|---|---|
| Pure DNase | SD | 3.4 | 46 |
| | SFD | 7.0 | 70 |
| DNase/mannitol 50/50 | SD | 6.1 | 14 |
| | SFD | 7.7 | 67 |
| DNase/trehalose 80/20 | SD | 2.9 | 29 |
| | SFD | 6.0 | 73 |
| DNase/trehalose 60/40 | SD | 2.6 | 36 |
| | SFD | 7.1 | 56 |
| DNase/trehalose 40/60 | SD | 3.2 | 20 |
| | SFD | 5.7 | 23 |
| DNase/sucrose 60/40 | SD | 2.8 | 27 |
| | SFD | 6.3 | 56 |
| Pure E25 | SD | 3.3 | 27 |
| | SFD | 7.7 | 50 |

TABLE 3-continued

Physical size and fine particle fraction of spray-dried and spray freeze-dried powders of rhDNase and anti-IgE antibody in formulation with different sugars.

| Formulation | Method | Median particle size ($\mu$m)[a] | Fine particle fraction (%)[b] |
|---|---|---|---|
| E25/mannitol/glycine 80/10/10 | SD | 3.8 | 25 |
|  | SFD | 8.0 | 45 |
| E25/mannitol 80/20 | SD | 4.0 | 29 |
|  | SFD | 11.0 | 40 |
| E25/trehalose 60/40 | SD | 3.3 | 31 |
|  | SFD | 5.9 | 52 |
| E25/mannitol/trehalose 60/20/20 | SD | 3.6 | 19 |
|  | SFD | 8.6 | 19 |

[a]Determined by Malvern particle size analyzer.
[b]Determined by multiple stage liquid impingement.

As observed with pure protein powders, spray freeze-dried powders outperformed spray-dried powders in aerosolization although their physical size were almost twice larger. However, there are a few exceptions: (i) 50/50 rhDNase/mannitol, (ii) 40/60 rhDNase/trehalose, and (iii) 60/20/20 E25/mannitol/trehalose.

In (i), the physical sizes of the two powder were almost equivalent. a significant change in particle shape and morphology suggests mannitol crystallization. Crystals growing between spray-dried particles (FIG. 8a) resulted in larger, fused particles which reduced powder dispersibility. Spray freeze-dried particles were highly deformed from sphericity (FIG. 8b) also due to mannitol crystallization but maintained excellent aerosol performance. In Case (ii), the spray freeze-dried powder (FIG. 8d) did not show better aerosol performance as compared to the spray-dried powder (FIG. 8c). In addition to trehalose's sticky nature (Maa et al., 1997), losing the characteristics of porosity for the spray freeze-dried particle might also be attributed to the reduction in powder dispersibility. In Case (iii), the spray-dried powder (FIG. 8e) shows the dimple morphology (Maa et al., 1997, supra). The shape of the spray freeze-dried particle (FIG. 8f) was highly deformed and appeared to have a crystalline character. It appears that the spray freeze-drying process promoted the tendency of mannitol crystallization.

Protein aggregation upon spray freeze drying

Excipient-free protein powders suffered significant aggregation upon spray freeze drying, 21.6% for rhMAb and 13.6% for rhDNase. However, the same excipient-free proteins, following a normal lyophilization process (freeze dried in vials), aggregated only slightly, 4.3% for rhMAb and 1.2% for rhDNase. This suggests that the additional spray-freezing operation presented a highly stressful event. The nature of the stress may be due to events such as the shear stress, the stress of air-water interface associated with air atomization, the stress of extremely fast freezing, and so on. Our previous studies concluded that shear and the shear stress associated with air atomization were low and had little influence on rhDNase, and that rhDNase was very stable at the air-liquid interface. The same was observed with rhMAb (data not published). Therefore, protein denaturation upon spray freeze drying mainly occurred during the fast freezing step.

Extremely fast freezing upon SFD Extremely fast freezing was achieved by subjecting a small volume ($5.2 \times 10^{-10}$ cm$^3$ for a droplet of 10 $\mu$m in diameter) into an extremely cold environment (liquid $N_2$ at $-196°$ C.). As mentioned earlier, the freezing time for 1-mL liquid in a vial in liquid $N_2$ was on the order of a few seconds. We derived a simple mathematical model to estimate the freezing time of a 10-$\mu$m droplet. The calculation suggested that the droplet froze in less than one millisecond, approximately 4 orders of magnitude faster than the freezing time for 1-mL liquid in the vial. It is well known that fast freezing generated a large surface area of freeze-dried solids (Chang et al. (1996) supra, Hsu et al. (1995) supra). SEM analysis of spray freeze-dried, excipient-free rhMAb and rhDNase powders shows a very porous structure. The characteristics of high porosity was confirmed by comparing the pore size distribution and the internal surface area of the spray freeze-dried particles with their freeze-dried counterparts. FIG. 9 shows the cumulative pore volume over a range of pore diameter (0.0013–0.0673 $\mu$m) for the excipient free rhDNase powders prepared by SFD and freeze drying. Their corresponding cumulative pore volumes, 0.23 and 0.0019 cc/g (<0.0673 $\mu$m), differed by 2 orders of magnitude. Their surface areas were also dramatically different, 121.2 m$^2$/g for the SFD powder and 1.4 m$^2$/g for the freeze-dried powder. The same result was observed for the excipient-free rhMAb where the surface area of SFD and freeze dried powders were 127.7 m$^2$/g and 1.7 m$^2$/g, respectively. The significantly increased surface area and pore volume for the SFD powder induced by fast freezing of this nature is consistent with the report (Hsu et al. (1995) supra) that the internal surface area of the freeze-dried cake increases with increasing freezing rate where the largest surface area was only around 2 m$^2$/g.

Effect of Cryoprotectants

Next, we examined the effect of addition of some common sugar excipients to the spray freeze-dried and freeze-dried protein formulations. Soluble aggregation and the internal surface area of these powders are tabulated in Table 4. Compared to excipient-free formulations, all sugar excipients protected the protein against aggregation to a great extend for the freeze-dried powders and to some extent for the SFD powders. RhDNase was better protected than rhMAb. When added to the spray freeze-dried rhMAb/trehalose formulation, PEG had no additional effect. Overall, the degree of aggregation was relatively high for the spray-freeze-dried rhMAb (e.g. ~15%) despite the protection by sugar excipients, suggesting that other mechanisms might be involved.

TABLE 4

Soluble protein aggregation and surface area of spray freeze-dried and freeze-dried powders of rhDNase and rhMAb formulations[a].

| Formulations | Spray freeze drying Aggregation (%) | Spray freeze drying Surface area (m$^2$/g) | Freeze drying Aggregation (%) |
|---|---|---|---|
| Excipient-free rhMAb | 21.6 | 127.7 | 4.3 |
| rhMAb:mannitol 80:20 | 20.8* | 121.6 | 0.2 |
| rhMAb:trehalose 60:40 | 14.6 | 74.6 | 0.3 |
| rhMAb:trehalose 60:40 + 2% PEG | 15.0 | 9.5 | 0.2 |
| Excipient-free rhDNase | 13.6 | 121.2 | 1.2 |
| rhDNase:trehalose 80:20 | 6.5 | 110.5 | 0.6 |
| rhDNase:trehalose 60:40 | 5.4 | 70.5 | 0.5 |
| rhDNase:trehalose 40:60 | 5.7 | 4.4 | 0.4 |
| rhDNase:mannitol 80:20 | 7.5* | 123.7 | 0.4 |
| rhDNase:mannitol 50:50 | 9.2* | 29.9 | 0.9* |
| rhDNase:mannitol 60:40 in 50 mM sodium phosphate (pH 6.0) | 7.2* | 11.1 | 0.5 |
| rhDNase:sucrose 60:40 | 6.3 | 41.5 | 0.5 |

[a]Spray drying and spray freeze drying conditions were described in the Method Section.
*Mannitol crystallized as determined by X-ray powder diffraction analysis.

Given that sugar excipients lose their protective function as a result of crystallization-induced phase separation, X-ray powder diffraction analysis was used to determine sugar crystallization. All but mannitol-containing formulations remained amorphous upon SFD (formulations with * in Table 4). Mannitol tends to crystallize upon freeze drying (Izutsu et al., *Pharm. Res.*, 10: 1232–1237(1993), Izutsu et al., *Chem. Pharm. Bull.*, 42: 5–8.(1994)) when its concentration in the solid exceeds 30% (dry basis). Interestingly, mannitol in the 80:20 rhMAb:mannitol formulation was amorphous upon freeze drying but crystallized upon SFD. Another example indicating that SFD promotes mannitol crystallization was the 60:40 rhDNase/mannitol formulation containing 50 mM sodium phosphate. As suggested by Izutsu et al. (1993) supra, Izutsu et al. (1994) supra, sodium phosphate at this concentration could inhibit mannitol from crystallization. This was confirmed for the freeze-dried sample, but SFD again promoted mannitol crystallization. Table 4 shows protein formulations containing crystallized sugar excipients were generally less stable compared to formulations where sugar excipients remained amorphous. Despite this, the physical state of the cryoprotectant alone cannot fully explain protein aggregation upon freezing during SFD.

Effect of Ice-water Interface (surface area)

The surface area (Table 4) varied from 4.4 $m^2/g$ to 127.7 $m^2/g$, suggesting that formulation affected the porosity of the SFD powders significantly. However, no clear trend was observed between the surface area and protein aggregation. For example, the powder of 40:60 rhDNase:trehalose had the smallest surface area (4.4 $m^2/g$), but its aggregation (5.7%) was comparable to that of the 60:40 rhDNase:trehalose powder which had a much higher surface area (70.5 $m^2/g$).

To compare powders with the same formulation but different surface areas, we prepared SFD powders (60:40 rhMAb:trehalose) using two types of atomization, air and ultrasound. As summarized in Table 5, air atomization at the atomizing air flow rates of 1050 and 600 L/hr, produced powders of 7 and 16 $\mu$m in medium diameter, but ultrasonic atomization resulted in the most coarse powder (32 $\mu$m). To examine the effect of the freezing rate, the powder's surface area and protein aggregation was plotted against (droplet diameter)$^{-2}$ (FIG. 11) because $1/R^2$ represented the freezing rate. The relationship between the surface area and the freezing rate is linear, surface area=43.2+1543×1/$R^2$, R=0.9996. This is consistent with the observation by Hsu, et al. (Hsu et al. (1995) supra) though our freezing rate and surface area were significantly higher. However, neither the surface area nor the freezing rate correlated linearly with protein aggregation mainly because ultrasonic atomization generated aggregate-free protein although this powder still had a large surface area (44.3 $m^2/g$). This result clearly suggests that denaturation at ice-water interface played a role, but was not the only factor.

TABLE 5

The effect of surface area of spray freeze-dried powders (60:40 rhMAb:trehalose) and surfactant on soluble protein aggregation.

| Atomization | Particle diameter ($\mu$m) | Surface area ($m^2/g$) | Aggregation (%) |
|---|---|---|---|
| Air at 1050 L/hr | 7 | 74.6 | 14.6 |
| Air at 600 L/hr | 19 | 49.9 | 9.3 |
| Ultrasonic | 32 | 44.3 | 0 |
| 0.05% Tween 20 Air at 1050 L/hr | 7 | 72.9 | 8.7 |

The role of ice-water interface was further examined using the rationale that adding a low molecular-weight surfactant, such as polysorbate 20, would occupy the ice-water interface and thus retard protein interfacial adsorption/denaturation. The formulation of rhMAb:trehalose containing 0.05% polysorbate 20 was spray freeze dried using air atomization at 1050 L/hr. The surface area of the powder remained unchanged compared to the surfactant-free powder. Even though the aggregate content decreased, the level of aggregation was still high (8.7%), again suggesting that denaturation at ice-water interface was not the only factor affecting protein stability.

Freeze/Thaw

The formulations presented in Table 5 were subjected to freeze/thaw stress. After spray freezing, the frozen powder was thawed at room temperature. Freezing and thawing resulted in white precipitates except for the surfactant-containing formulation which was clear. Little soluble aggregates were detected in either of the samples; protein loss to precipitation was significant for the surfactant-free solutions atomized by air at 1050 L/hr (29% loss), whereas the protein formulated with polysorbate was completely recovered. This result suggests thawing added an additional stress to the protein that occurred mainly at the ice-water interface, and this stress could effectively be protected by surfactant. When the surfactant-containing formulation was dried instead of being thawed, it resulted in 8.7% of aggregates (Table 5). Therefore, the unknown stress that caused protein denaturation upon extremely fast freezing was reversible upon stress relaxation, i.e. thawing. However, denaturation of stressed protein molecules became permanent after being dried.

Given the data on the effect of surface area and freeze/thaw on protein aggregation, a freezing-related stress event, arising possibly from a shear stress associated with phase separation between ice and freeze concentrate, might be most responsible for protein denaturation upon SFD. This freezing stress generated at the freezing front (ice-water interface) has an adverse effect on the two model proteins only at a freezing rate beyond a critical point, in the range of $8.4\times10^{-4}$ and $3.4\times10^{-3}$ sec (for droplet diameter between 16 and 32 $\mu$m). When the ice front advances faster than this critical rate, it might alter protein conformation which leads to aggregation upon drying. However, it appears that these conformational changes are reversible upon relaxation of the stress by thawing. To test this hypothesized mechanism, we performed a series of experiments to anneal the spray-frozen powder of 60:40 protein:trehalose at temperatures(−5°, −10°, and −15° C.) higher than the primary drying temperature (−25° C.) for one hour before the lyophilization cycle began. Table 6 summarizes the effect of this annealing process on the powder's surface area and on protein aggregation. Both the surface area and protein aggregation decreased upon annealing. The higher the annealing temperature, the smaller the surface area and the lower the aggregate content. Annealing at temperatures close to the melting point caused ice crystals to fuse into larger crystals, thereby reducing the surface area of the particle. For example, annealing at −5° C. resulted in a significant surface area reduction (8.3 $m^2/g$ for rhMAb). Based on our earlier conclusion that surface area played only a limited role, the reduction in aggregation from 14.6% to 2.1% could be attributed to the relaxation of the proposed stress.

TABLE 6

The effect of freeze/thaw for the protein solution (10 mg/mL) of 60:40 rhMAb:trehalose on soluble protein aggregation.

| Atomization | Soluble aggregation (%) | Protein loss as insoluble aggregate (%) |
| --- | --- | --- |
| Air at 1050 L/hr | 0.6 | 29 |
| Air at 600 L/hr | 0 | 9 |
| Ultrasonic | 0 | 3 |
| 0.05% Tween 20 Air at 1050 L/hr | 0 | 1 |

Example 2

Spray Freeze Drying of IGF-I

Preparation of recombinant humanized insulin-like growth factor formulations. Recombinant humanized insulin-like growth factor (rhIGF-I), a molecular weight of 7,648 Dalton, was produced at Genentech from two different sources. The current liquid product, containing of 10 mg rhIGF-I/mL, 100 mM sodium chloride, 50 mM sodium acetate, 0.9% benzyl alcohol, 0.2% polysorbate 20 at pH 5.4, was buffer-exchanged in 10 mM histidine (pH 5.5), and was concentrated to a protein concentration of 17.7 mg/mL. The second source was from S-Sepharose pool containing 15–25 mg/mL of rhIGF-I in 200 mM citrate at pH 6.0. This pool was first buffer-exchanged into 200 mM sodium chloride, 230 mM L-arginine and 10 mM histidine (pH 7.3) to remove citrate. It was then diafiltered into 230 mM L-arginine and 10 mM histidine (pH 7.3) and concentrated to a protein of concentration of 30 mg/mL. All formulations were prepared using ultrafiltration/diafiltration, followed by the additions of excipients.

Varying amounts of carbohydrates (trehalose or mannitol) and amino acids (histidine and/or Larginine) were used to prepare inhalation formulations as follows:

(a) Current liquid product (see above for detail);
(B) rhIGF-I, 10 mM histidine, pH 5.5;
(C) rhIGF-I, 10 mM histidine, 230 mM L-arginine, pH 7.3;
(D) rhIGF-I:trehalose @ 60:40 (weight ratio), 10 mM histidine, pH 5.5;
(E) rhIGF-I:trehalose @ 60:40 (weight ratio), 10 mM histidine and 230 mM L-arginine pH 7.4.

Ultrafiltration (UF)/Diafiltration (DF)

UF/DF was performed on a bench-top tangential flow filtration (TFF) system (stainless steel Pellicon-2™, Millipore) with a 5 kD regenerated cellulose membrane cassettes (type C screen) with a membrane area of 0.1 m². Eight diavolumes were used in the diafiltration step. Diavolume is defined as the passage of a quantity of buffer equivalent to the volume of retentate (Chang et al. (1996) supra). The experiments were conducted at constant retentate pressure of 18 psi, feed flow rate of 0.5 L/min and at ambient temperature. Some UF/DF runs were performed in a fully automated TFF system. Details of the system has been described elsewhere (Townsend et al. (1988) supra).

Spray freeze drying This was done as outlined above. The spray freeze-dried IGF-1 powders were prepared using a two-fluid nozzle (from a Büchi 190 spray dryer) for atomization. A 3-L two-neck, round-bottom flask was filled with liquid nitrogen and was submerged in a container also containing liquid $N_2$. The liquid $N_2$ in the flask was agitated using a magnetic stirrer bar. The nozzle was pointed into the flask in the central neck which was wrapped with a heating tape to avoid nozzle head freezing. The protein liquid was atomized using an atomizing air flow rate of 1050 L/hr. Sprayed droplets froze upon contacting liquid $N_2$ The liquid feed rate was 10 mL/min for air atomization. After spraying, the whole content in the flask was poured into a metal tray and placed in a lyophilizer(GT20) which had been pre-chilled to −50° C. After a hold period of one hour at −50° C., vacuum was applied to the chamber. The shelf temperature was increased to −25° C. over a two-hour period and held for 40 hours. During secondary drying, the shelf temperature was increased to 20° C. over a four-hour period and was held for another 20 hours.

Dispersibility Measurement

The spray freeze-dried powder was blended with 100M lactose coarse carrier at 1:10 weight ratio of active rhIGF-I to coarse carrier by mixing (Turbula, Glenn Mill) and sieving (250-μm mesh). Ten individuals of pre-weighted samples of 10 mg blended powder (or 5 mg raw powder) were loaded into a dry powder inhaler (Dura Pharmaceuticals, San Diego) and dispersed into a multi-stage liquid impinger (MSLI) at an air flow rate of 60 L/min and an inhalation time of 5 seconds, as outlined above. The MSLI throat piece was attached to the top of the first stage. A filter paper was placed underneath stage 4 to capture fine particles in range of less than 1 μm. The material which deposited in the throat piece and the filter and their washings analyzed for protein content. The fine particle fraction is defined as powder with an aerodynamic mass median diameter of less than 6.8 μm, and was determined by the percentage of protein which deposited on stages 3, 4 and the filter.

The moisture content, SEMs, and particle size analysis were all done as outlined above.

Storage Conditions. Samples were stored in open glass vials inside sealed desiccators which contained saturated salt solution to control the humidity: calcium chloride at 38% relative humidity (rh). Temperatures were maintained by placing the sealed containers in constant, controlled temperature storage cabinets. Samples of both raw powders and formulated blends were stored at 2–8° C. and at 30° C. The powders were assayed for soluble aggregates, oxidation, and aerosol performance at t=0, 4 weeks, and 24 weeks of storage.

Particle Size and Moisture Content. Table 7 summarizes the particle size and the size distribution (span) of the spray freeze-dried rhIGF-I powders (Form. a-E).

TABLE 7

Summary of Physical Characterization of rhIGF-I Powders

| Formulation | Particle Size[c] (μm) | Span |
| --- | --- | --- |
| Spray-freeze dried | — | — |
| a | 8.9 | 3.5 |
| B | 2.6 | 4.2 |
| C | 6.8 | 1.7 |
| D | 3.7 | 1.1 |
| E | 6.1 | 1.4 |

[a]Measurement was not done immediately off the spray dryer. Powders were stored in focal tubes, and caked out during storage at ambient conditions. Therefore, they were not dispersed well in the dispersant.
[b]There was impurity present in the measurement.
[c]The volume median diameter is the diameter above and below which 50% of the volume distribution lies. The span = [D(v, 90) − D(V, 10)]/D (v, 50) where D(v, 90), D(v, 10) and D(v, 50) are the diameters of 90, 10 and 50% cumulative volume, respectively.

Protein Stability The effect of spray drying on protein aggregation and oxidation was investigated by size exclusion and reverse phase HPLC. The protein quality in all formulations except Form. D remained unchanged upon spray drying (data not shown). rhIGF-I in Form. D suffered approximately 2% of aggregation; therefore, the further investigation on this formulation was discontinued.

Aerosol Performance (Fine Particle Fraction) The spray-freeze dried powder was blended with 100 M lactose carriers prior to fine particle fraction (<6.8 μm) measurement using a multi-stage liquid impinger model. Blending can theoretically improve the fine powder's flow properties. Small particles tend to interact with themselves (agglomeration) and with any contact surfaces due to high surface energy. Agglomerated particles behave like large particles and are difficult to be dispersed. Sticking to other contact surfaces results in material loss and poor powder flowability. If the interaction between the spray-dried particle (raw powder) and the carrier particle ($F_{r-c}$) overcomes the interaction among the raw powder ($F_{rr}$), it can result in homogeneous blending, thereby enhancing the powder's flowability. The next hurdle to jump is that these fine particles should be able to be deagglomerated from the carrier particle upon inhalation, i.e. the inhalation force can overcome $F_{r-c}$. Factors affecting these interactions are highly complicated.

At t=0 (before storage), the fine particle fraction of the powder was highly depending upon protein formulation, ranging from 13% to 71% (Table 8).

TABLE 8

Summary of Physical Properties with Respect to Fine Particle Fraction of rhIGF-I Blends/Raws Stored at 38% RH

| | | Fine Particle Fraction (%) | | | |
|---|---|---|---|---|---|
| | | t = 4 weeks | | t = 24 weeks | |
| Formulation | t = 0 | 2–8° C. | 30° C. | 2–8° C. | 30° C. |
| Spray-freeze dried | | | | | |
| D | 37 | — | — | — | — |
| E | 71 | 63 | 66 [85] | 83 [82] | 75 [92] |
| G | 13 | — | — | — | — |
| I | 61 | 59 | 69 | 73 [79] | 63 [79] |
| L | ND | | | | |

[a]Dispersion data of raw powder.
ND Not determined.

Powders with a high FPF (>40%) showed a homogenous blending.

Five formulations (A, B, C., D and E) were tested for preparing spray freeze-dried rhIGF-I powders. Spray freeze drying produced large, porous particles with significantly improved aerosol performance compared to spray-dried powders (data not published). The size of these powders were indeed larger than their spray-dried counterpart (data not shown). We selected Form. B & D for further investigation because the arginine-containing powders (Form. C & E) collapsed upon storage in the vials and rhIGF-I aggregated (around 6%) in Form A. The FPF of the powders (Form. B & D) almost tripled compared to their spray-dried counterpart. After storage at 2–8 and 30° C. up to 6 months, the aerosol performance of the blended powders either remained unchanged or became slightly better. Another interesting finding is that the nonblended (raw) powder had a better dispersibility than the blended powder, which was opposite to the spray-dried powder. This suggests that spray freeze drying produced aerosol powders of very different aerodynamic properties.

We claim:

1. A method of preparing a spray-freeze dried composition for pulmonary administration comprising particles of a therapeutic protein having an average physical size of 6–8 microns and an aerodynamic particle size of less than 6.8 microns, said method comprising:

(a) atomizing a liquid formulation comprising a therapeutic protein followed by freezing, wherein the freezing is accomplished by immersion into a cold fluid to prepare frozen droplets;

(b) annealing said frozen droplets;

(c) drying said droplets to form powder particles; and (d) recovering said particles;

wherein said annealing occurs prior to said drying.

2. The method of claim 1 wherein the temperature of the cold fluid ranges from about –200° C. to –80° C.

3. The method of claim 1 wherein the temperature of the cold fluid ranges from about –200° C. to about –100° C.

4. The method of claim 3 wherein the temperature of the cold fluid is about –200° C.

5. The method of claim 3 wherein the temperature of the cold fluid is about –196° C.

6. The method of claim 5 wherein the cold fluid is liquid nitrogen.

7. The method of claim 1 wherein the drying step is done at about the same temperature as the freezing step.

8. The method of claim 1 wherein the annealing is done at a temperature from about –10° C. to about –80° C.

9. The method of claim 8 wherein the annealing is done at a temperature from about –30° C. to about –60° C.

10. The method of claim 9 wherein the annealing is done at a temperature of about –50° C.

11. The method of claim 10 wherein the drying is done under a vacuum and at a temperature from about –10° C. to about –50° C.

12. The method of claim 11 wherein the drying temperature is from about –20° C. to about –40° C.

13. The method of claim 12 wherein the drying temperature is at about –25° C.

14. The method of claim 10 wherein the drying is done to achieve a dryness of about 1–10% remaining water.

15. The method of claim 14 wherein the dryness is about 1 to about 5% remaining water.

* * * * *